United States Patent
Kumar

(10) Patent No.: US 12,137,807 B1
(45) Date of Patent: Nov. 12, 2024

(54) IMAGE CAPTURING FOOT CARE APPARATUSES AND CAMERA MOUNTING DEVICES THEREFOR

(71) Applicant: Amit Kumar, Chino Hills, CA (US)

(72) Inventor: Amit Kumar, Chino Hills, CA (US)

(*) Notice: Subject to any disclaimer, the term of this patent is extended or adjusted under 35 U.S.C. 154(b) by 114 days.

(21) Appl. No.: 17/960,879

(22) Filed: Oct. 6, 2022

Related U.S. Application Data

(60) Provisional application No. 63/366,775, filed on Jun. 22, 2022.

(51) Int. Cl.
| | |
|---|---|
| *A47C 16/02* | (2006.01) |
| *A61B 5/00* | (2006.01) |
| *G03B 17/56* | (2021.01) |
| A45D 44/00 | (2006.01) |
| F16M 11/06 | (2006.01) |

(52) U.S. Cl.
CPC ............ *A47C 16/02* (2013.01); *A61B 5/0077* (2013.01); *G03B 17/561* (2013.01); *A45D 44/00* (2013.01); *A45D 2044/007* (2013.01); *F16M 11/06* (2013.01)

(58) Field of Classification Search
CPC ...... G03B 17/561; A47C 16/02; A61B 5/0077
See application file for complete search history.

(56) References Cited

U.S. PATENT DOCUMENTS

| | | | |
|---|---|---|---|
| 5,181,613 A | 1/1993 | Wright | |
| 7,232,265 B1* | 6/2007 | Price | F16M 11/2021 396/428 |
| 7,857,268 B2* | 12/2010 | Chiu | F16M 11/041 248/206.3 |
| 9,095,207 B2* | 8/2015 | Schindler | A47B 5/02 |
| 9,723,930 B2 | 8/2017 | Burch et al. | |
| 10,178,209 B1* | 1/2019 | Hesse | H04N 23/54 |
| D852,421 S | 6/2019 | Solitt | |
| 10,993,655 B2 | 5/2021 | Swerdlow | |
| 2008/0296447 A1 | 12/2008 | Peterson | |
| 2014/0049088 A1 | 2/2014 | Appiah Finn | |
| 2017/0086559 A1 | 3/2017 | Mulroy | |
| 2021/0227949 A1* | 7/2021 | Kumar | A45D 29/22 |

* cited by examiner

*Primary Examiner* — Milton Nelson, Jr.
(74) *Attorney, Agent, or Firm* — R. Keith Harrison

(57) ABSTRACT

A foot care apparatus suitable for imaging a foot of a user may include a support stand. A footrest may be supported by the support stand. The footrest may be configured to support the foot of the user. A tray may extend from the footrest. A camera mount device may be supported by the tray. The camera mount device may be configured to hold an electronic device having a camera with the camera facing the footrest. The footrest, the tray and the camera mount device may be disposed within an imaging plane. The support stand may be adjustable such that the imaging plane coincides with a horizontal plane or slopes with respect to the horizontal plane upwardly from the footrest to the camera mount device.

15 Claims, 26 Drawing Sheets

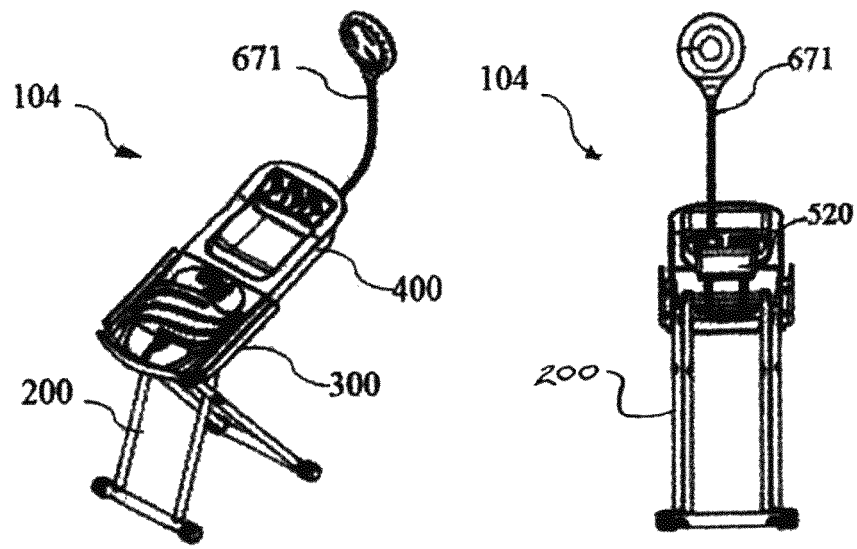
FIG. 10
FIG. 11
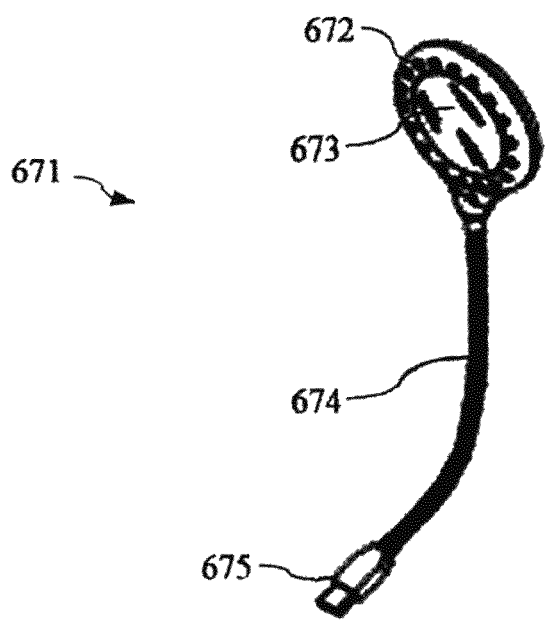
FIG. 12

IMAGE CAPTURING FOOT CARE APPARATUSES AND CAMERA MOUNTING DEVICES THEREFOR

CROSS-REFERENCE TO RELATED APPLICATIONS

This application claims the benefit of U.S. provisional application No. 63/366,775, filed Jun. 22, 2022, and entitled IMAGE CAPTURING FOOT CARE APPARATUS, which provisional application is hereby incorporated by reference herein in its entirety.

FIELD

Illustrative embodiments of the disclosure relate to foot care apparatuses used for foot inspection, treatment and maintenance. More particularly, illustrative embodiments of the disclosure relate to image capturing foot care apparatuses which can be used to facilitate comfortable and effective foot inspection, treatment, maintenance and imaging with or without out assistance from others, and camera mounting devices for image capturing foot care apparatuses.

BACKGROUND

The background description provided herein is solely for the purpose of generally presenting the context of the illustrative embodiments of the disclosure. Aspects of the background description are neither expressly nor impliedly admitted as prior art against the claimed subject matter.

Self-inspection of one's own foot, particularly the inaccessible parts of the foot such as the sole, heel, arch or instep, is typically a difficult undertaking. However, inspection and maintenance of the foot is important for health as well as hygienic reasons. Regular foot care is especially important for those who suffer from foot diseases such as infections and wounds caused by diabetes or other conditions.

As per the article published by National Center for Biotechnology Information (NCBI) of National Institute of Health (NIH), a part of the U.S. Department of Health and Human Services, (https://www.ncbi.nlm.nih.gov/pmc/articles/PMC6238864/), diabetes affects 1 in 10 people worldwide. One of the most devastating potential consequences of diabetes is the loss of a limb (lower extremity amputation) due to complications resulting from a diabetic foot ulcer (DFU). Diabetic patients have a lifetime risk of 15% to 25% of developing a DFU, which can lead to significant decrease in the quality of life due to limitations in mobility, function and independence, as well as increase in susceptibility to depression and anxiety. Moreover, DFUs and lower extremity amputations can lead to loss of livelihood.

Patients having foot conditions, therefore, need to inspect their feet regularly, although doing so is difficult even for normal people and more so for individuals who aren't flexible, such as the disabled and aged. Those who live alone may require the assistance of others to inspect their feet for them. For diabetic patients, good practice requires daily foot inspection before going to bed each night. This inspection routine may prevent an out-of-control infection from developing quickly over several days.

Diabetics afflicted with neuropathy may have partial or full loss of sensation at the bottom of one or both of their feet. Many times, neuropathy disorder may prevent such patients from feeling a sore as it develops in the foot in its early stages. Visually checking for sores, blisters, or anything unusual early, when there is only redness or slight drainage, may facilitate early discovery which leads to a doctor visit. Alternatively, pictures and/or videos of the afflicted area may be shared with doctors or health care service providers for medical advice before a deep infection develops. A patient with neuropathy may need to inspect the feet on a regular basis to watch for any problems which may potentially develop at the bottom of one or both feet. Because the feet are at the opposite end of the body, however, thorough self-inspection of the feet may be difficult or impossible without the patient's being a master contortionist. Moreover, age and our eyesight changes may render visualization of the bottom of the foot a major problem.

Thorough visualization of the foot and leg of a patient by healthcare workers as the patient is treated in a clinic or hospital may also be an issue in activities such as administration of medication, physiotherapy, management of bandages and plaster casts, etc. Easy and convenient access of the foot for visibility in treatment in a comfortable posture for the patient may be critical for proper treatment of the patient.

Daily foot infection without using a comfortable visualization apparatus may be a difficult process. Utilization of an apparatus which is easily accessible and has a foot stand or support with a mirror and/or a camera such as that in a smart phone on the bed side can be used to obtain optimum viewing of all the parts of the foot by the patient in a home setting may be needed for patients with foot diseases or wounds.

In addition to a comfortable foot stand and mirror, very often a patient may require immediate medical help, assistance, medication or treatment depending on the seriousness or severity of the condition. In some cases, frequent visitations to a doctor, clinic or hospital may not be possible. Thus, sharing pictures, videos and/or audio messages which relate to the foot condition with healthcare providers may be advantageous.

Accordingly, a need exists for image capturing foot care apparatuses which can be used to facilitate comfortable and effective foot inspection, treatment, maintenance and imaging with or without out assistance from others, and camera mounting devices for image capturing foot care apparatuses.

SUMMARY

Illustrative embodiments of the disclosure are generally directed to image capturing foot care apparatuses which can be used to facilitate comfortable and effective foot inspection, treatment, maintenance and imaging with or without out assistance from others. An illustrative embodiment of the image capturing foot care apparatuses may include a support stand. A footrest may be supported by the support stand. The footrest may be configured to support the foot of the user. A tray may extend from the footrest. A camera mount device may be supported by the tray. The camera mount device may be configured to hold an electronic device having a camera with the camera facing the footrest. The footrest, the tray and the camera mount device may be disposed within an imaging plane. The support stand may be adjustable such that the imaging plane coincides with a horizontal plane or slopes with respect to the horizontal plane upwardly from the footrest to the camera mount device.

In some embodiments, the foot care apparatus may include a support stand. A footrest may be supported by the support stand. The footrest may be configured to support the foot of the user. A tray may extend from the footrest. A camera mount device may include a device mount assembly supported by the tray. A camera mount bracket may be supported by the device mount assembly. The camera mount bracket may be configured to hold an electronic device having a camera with the camera facing the footrest.

The preceding and following embodiments and descriptions are for illustrative purposes only and are not intended to limit the scope of this disclosure. Other aspects and advantages of this disclosure will become apparent from the following detailed description.

BRIEF DESCRIPTION OF THE DRAWINGS

Embodiments of the present disclosure are described in detail below with reference to the following drawings. These and the other features, aspects, and advantages of the present disclosure will become better understood with regard to the following description, appended claims, and accompanying drawings, the drawings described herein are for illustrative purpose only of the selected embodiments and not all possible implementations and are not intended to limit the scope of the present disclosure.

FIG. 10 is a perspective view of another illustrative embodiment of the image capturing foot care apparatus with mirror or magnifying lens and light combo attached to the tray of the apparatus.

FIG. 11 is a rear view of the illustrative foot care apparatus illustrated in FIG. 10.

FIG. 12 is a perspective view of the mirror or magnifying lens and light combo of the illustrative foot care apparatus illustrated in FIG. 10.

DETAILED DESCRIPTION

Figure 1:
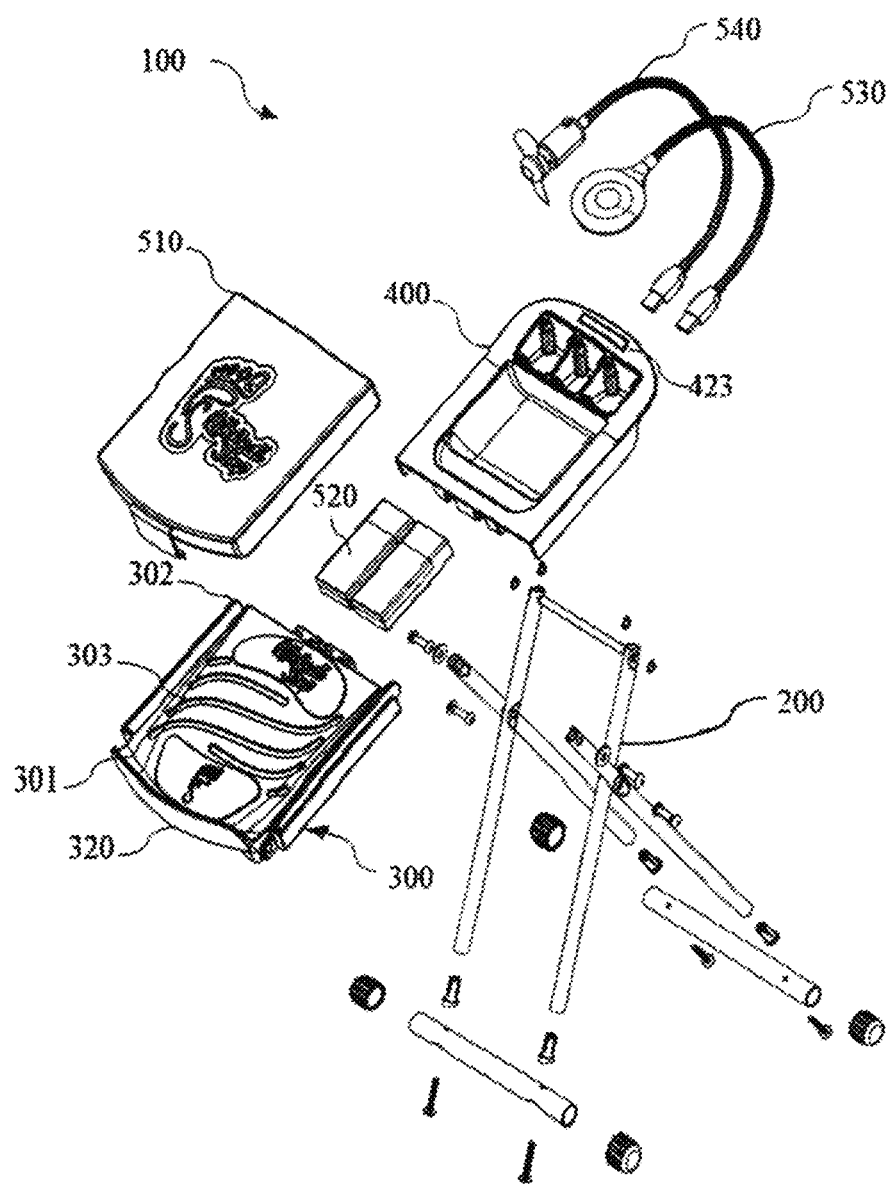
FIG. 1 is an exploded perspective view of an exemplary foot care apparatus suitable for implantation of the camera mounting devices of the present disclosure.

The phrases "in one embodiment," "in various embodiments," "in some embodiments," and the like are used repeatedly. Such phrases do not necessarily refer to the same embodiment. The terms "comprising," "having," and "including" are synonymous, unless the context dictates otherwise. Such terms do not generally signify a closed list. "Above," "adhesive," "affixing," "any," "around," "both,"

"bottom," "by," "comprising," "consistent," "customized," "enclosing," "friction," "in." "labeled," "lower," "magnetic." "marked." "new." "nominal." "not," "of," "other," "outside," "outwardly," "particular," "permanently." "preventing." "raised." "respectively," "reversibly," "round." "square," "substantial," "supporting," "surrounded," "surrounding," "threaded," "to," "top," "using." "wherein," "with," or other such descriptors herein are used in their normal yes-or-no sense, not as terms of degree, unless context dictates otherwise.

Reference is now made in detail to the description of the illustrative embodiments as illustrated in the drawings. While illustrative embodiments are described in connection with the drawings and related descriptions, there is no intent to limit the scope of the disclosure to the embodiments disclosed herein. In alternate embodiments, additional devices, or combinations of illustrated devices, may be added to, or combined, without limiting the scope to the embodiments disclosed herein.

FIG. 1 illustrates an exemplary foot care apparatus 100 which is suitable for implantation of the camera mounting devices of the present disclosure. The foot care apparatus 100 may be used for number of applications and enables easy, convenient, and comfortable access to foot and toes of a patient with the capability to facilitate adjustable height and inclination or tilt of the foot for purposes including but not limited to foot maintenance, nail clippings, nail grooming, foot treatments, placement of footwear on the foot, tying of shoelaces, etc., at home without the help or aid of other people. The foot care apparatus 100 has many features that may include but are not limited to a foldable support stand 200 which may have adjustable height and inclination/slope options. The foot care apparatus 100 may have a detachable tray 400 with a nail and cuticle collecting compartment for collection and easy disposal of toenails; a storage compartment for nail grooming cosmetics such as nail paint, polish, paint remover and the like; side storage slots or grooves for tools such as clippers, tiles, scissors and the like; a detachable battery bank 520 with power ports to supply power to fans, lights, cameras and electric tools; and a separatable storage box 510 to facilitate storage of the tools and cosmetics during and after use. The foot care apparatus 100 may include options to hold a smart device such as a mobile phone, tablet, mobile battery bank etc. The mobile battery bank 520 may be used to power the fans, lights, camera and power tools, for foot care, inspection and treatment.

In some embodiments, the foot care apparatus 100 may have a design which is the same as or similar to that disclosed in U.S. patent application Ser. No. 17/231,045 (Pub. No. US 2021/0227949 A1), filed Apr. 15, 2021, which patent application is hereby incorporated by reference herein in its entirety. In some embodiments, the foot care apparatus 100 may have alternative designs. As shown in FIG. 1, the foot care apparatus 100 may include a support stand 200, a footrest 300, a tray 400, a storage box 510, one or more battery banks 520, a light with magnifying lens 530, a fan 540, and a holder slot 423 for a mobile electronic device. The footrest 300, the tray 400, the storage box 510, the battery banks 520, the light 530 and the fan 540 may be configured to be detachably coupled together and rest on the adjustable, foldable support stand 200.

Figure 2:
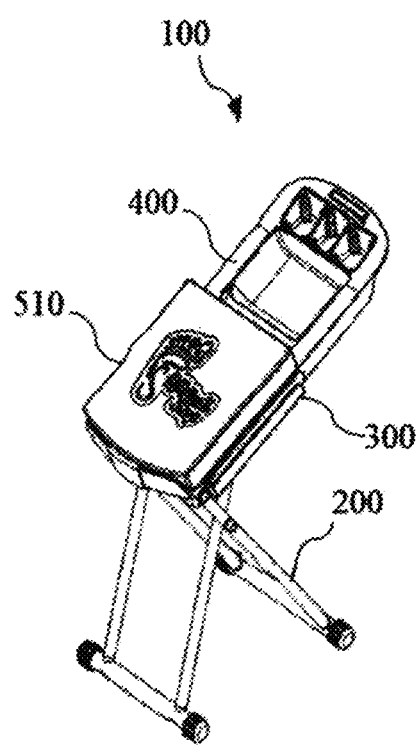
FIG. 2 is a perspective view of the assembled foot care apparatus illustrated in FIG. 1, deployed in an extended, functional configuration, with a storage box on the footrest of the apparatus.

FIG. 2 is a front perspective view of the of an exemplary foot care apparatus 100 for foot maintenance, with the storage box 510 attached to the footrest 300. As illustrated in FIG. 1, the footrest 300 may have a first end 301, a second end 302 and a top 303. A heel rest 320 may be provided at the first end 301 of the footrest 300. The storage box 510 may be removably placed on top of the foot rest 300 and attached to the heel rest 320.

Figure 3:
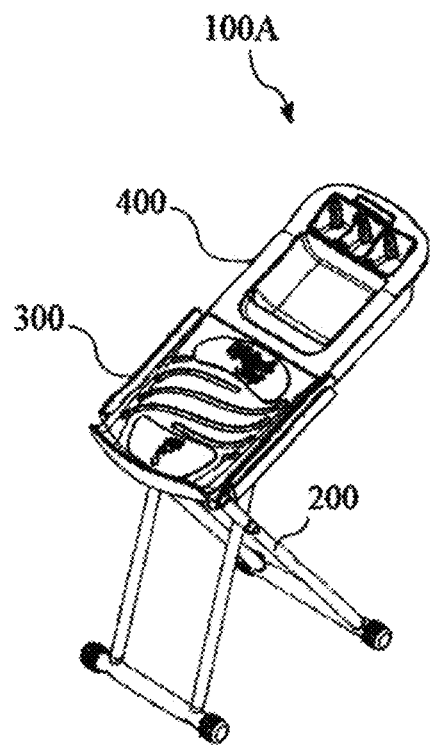
FIG. 3 is a perspective view of the assembled foot care apparatus illustrated in FIG. 1, with the storage box (not illustrated) removed from the footrest.

FIG. 3 is a front perspective view of the illustrative foot care apparatus 100 for foot maintenance, in which the storage box 510 is detached from the footrest 300.

Figure 4:
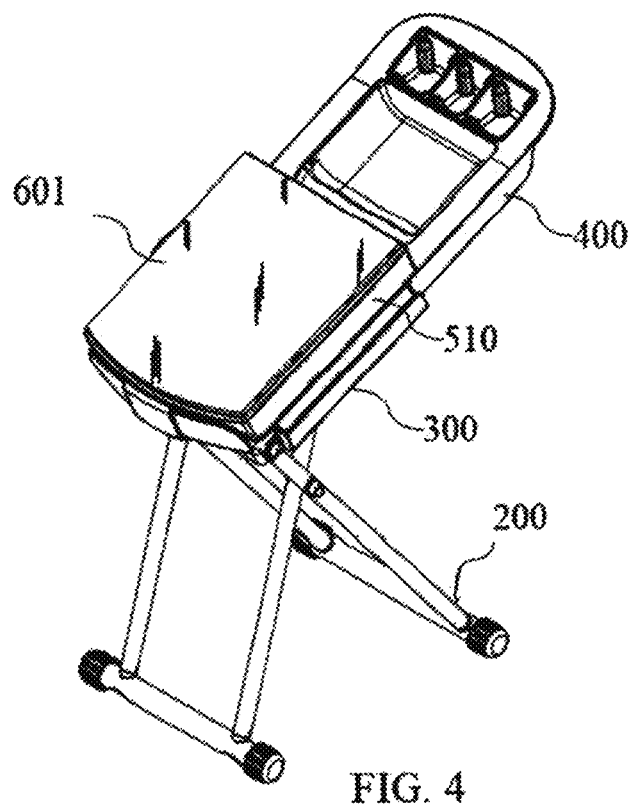
FIG. 4 is a perspective view an illustrative embodiment of an image capturing foot care apparatus, with a mirror attached to the storage box of the apparatus using an adhesive.

Referring to FIG. 4, in some embodiments, the foot care apparatus 101 may include a mirror 601. The mirror 601 may be attached to the top surface of the storage box 510 using an adhesive (not illustrated). Accordingly, a patient or user of the foot care apparatus 100 may place a foot over the mirror 601 and twist or bend the foot as required to view the refection of the portion of the foot which is otherwise difficult to view in the mirror 601.

Figure 5:
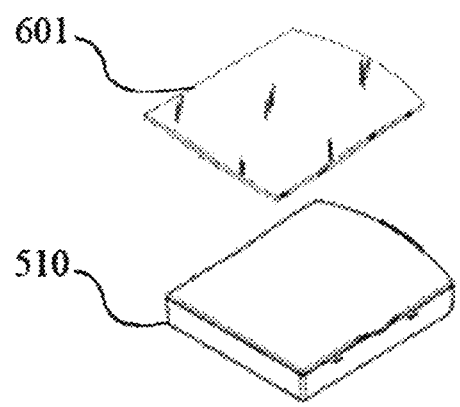
FIG. 5 is an exploded perspective view of the mirror detached from the storage box of the illustrative image capturing foot care apparatus illustrated in FIG. 4.

FIG. 5, is an exploded view of the storage box 510 and the mirror 601 of the foot care apparatus 101.

Figure 6:
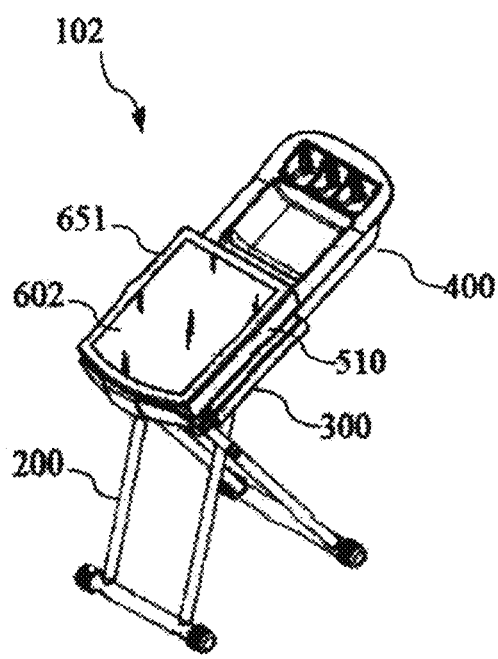
FIG. 6 is a perspective view of an exemplary unfolded foot care apparatus with the mirror fixed to the storage box by bracing.

Referring next to FIG. 6 of the drawings, in another illustrative embodiment of the foot care apparatus 102, the mirror 602 may be fixed on the top of the storage box 510 of the foot care apparatus 102. The mirror 602 may be fixed in place on the storage box 510 with a bracing 651. The mirror 602 may be slightly larger than the inner dimensions of the bracing 651 such that the bracing 651 holds the mirror 602 firmly with the bracing 651 overlapping the mirror 602.

Figure 7:
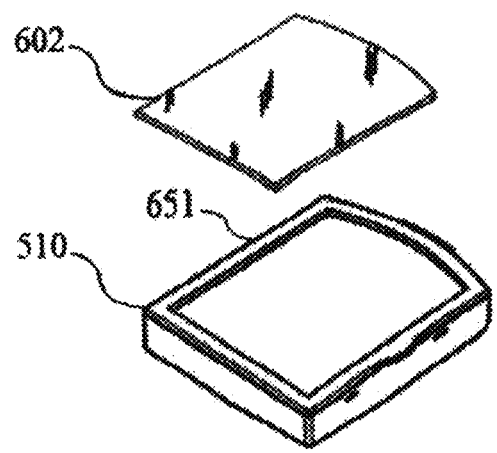
FIG. 7 is an exploded perspective view of the mirror detached from the storage box of the illustrative image capturing foot care apparatus illustrated in FIG. 6.

FIG. 7 is an exploded perspective view of the mirror 602 and the storage box 510 with the bracing 651.

Figure 8:
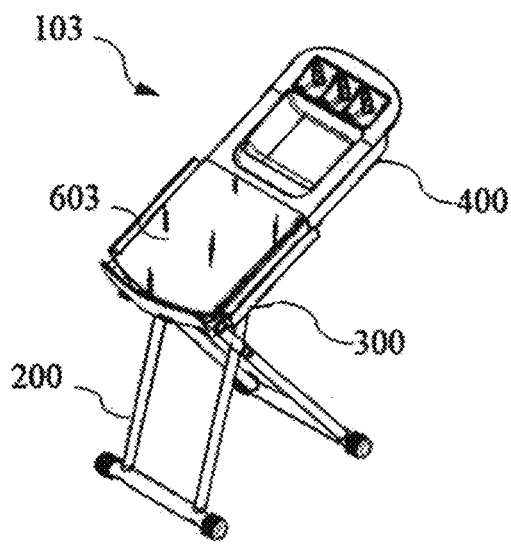
FIG. 8 is an exploded perspective view of another illustrative embodiment of the foot care apparatus without a storage box on the footrest and with the mirror fixedly attached to the footrest.

In some embodiments of the present disclosure, shown in FIG. 8, the mirror 603 may be installed directly over the footrest 300 via a plurality of coupling tabs 652 and 653. For each coupling tab 652, there may be a corresponding opening 654 on the footrest 300. There may also be a corresponding opening 655 on the heel rest 320 of the foot care apparatus 103.

In some embodiments, the mirror 603 may extend over the tray 400, partially or completely covering the entire tray 400 or extended further with or without additional coupling tabs 652 and corresponding openings 654 in the tray 400.

In some embodiments, the mirror 603 may be used without the tray 400, with the tray 400 detachable from the footrest 300.

Figure 9:
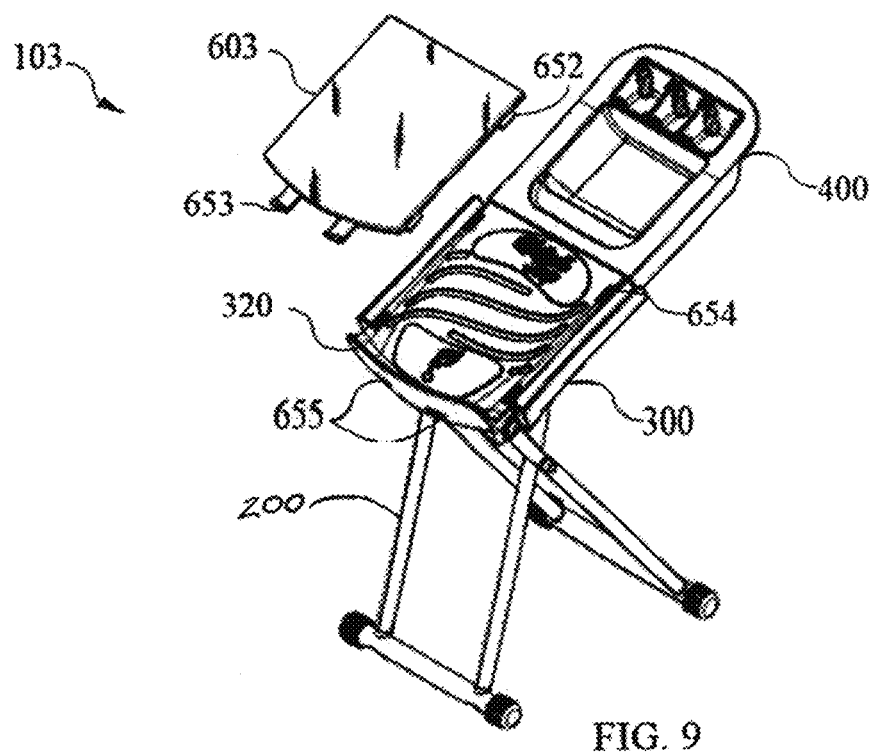
FIG. 9 is an exploded perspective view of the illustrative image capturing foot care apparatus illustrated in FIG. 8.

FIG. 9 shows an exploded view of the mirror 603 detached from the footrest 300 of the foot care apparatus 103, with a detailed view of the coupling tabs 652, 653 of the mirror 603 and the corresponding openings 654 and 655 in the foot care apparatus 103.

Referring to FIGS. 10 and 11, in some embodiments, a mirror or magnifying lens/light assembly 671 may be provided on the foot care apparatus 104. In some embodiments, the assembly 671 may include a mirror or a magnifying lens and a light.

Referring to FIG. 12, in some embodiments, the mirror or magnifying lens/light assembly 671 may include a mirror or magnifying lens 673 which may be surrounded by a series of LED lights 672. The mirror or magnifying lens/light assembly 671 may be powered up by connection to a battery bank 520 via a USB port 675 or any other compatible port. Further, the mirror or magnifying lens/light assembly 671 may be provided with a gooseneck 674 which enables the assembly 671 to positionally adjust and focus the assembly 671 to any part of the foot placed over the foot rest 300 to capture better vision of the foot or portion or area of interest on the foot.

Figures 13, 14:
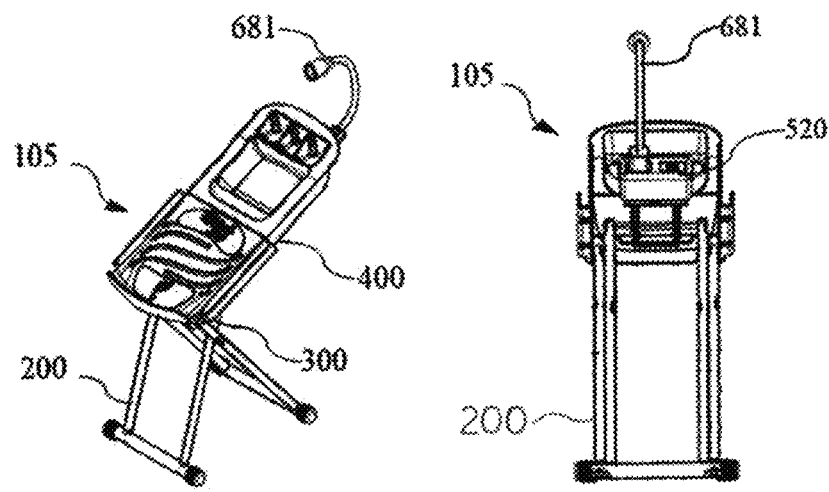
FIG. 13 is a perspective view of another alternative illustrative embodiment of the foot care apparatus with a camera and gooseneck with USB port attached to the tray of the apparatus.
FIG. 14 is a rear view of the illustrative foot care apparatus illustrated in FIG. 13.
Figure 15:
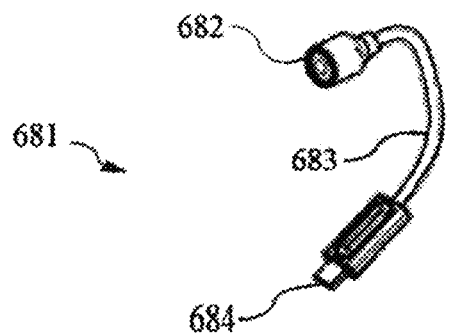
FIG. 15 is a perspective view of the camera and gooseneck with USB port illustrated in FIG. 14.

Referring next to FIGS. 13-15 of the drawings, in some embodiments, a smart digital camera 681 may be provided on the foot care apparatus 105. As illustrated in FIG. 15, the camera 681 may include a lens with control unit 682 on one end of a gooseneck 683. A USB or other port 684 may be provided on the opposite end of the gooseneck 683. The camera 681 may be powered up by connecting the USB or other port 684 to the battery bank 520. The gooseneck 683 may enable positional adjustment of the lens with control unit 682 with respect to the foot of the patient to focus the camera 681 to any part of the foot as the foot rests on the foot rest 300.

In some embodiments, the camera 681 may be controlled by a software application or may be installed in a mobile phone, computer, tablet or any other type of electronic device which is capable of running the software application. The software application may be provided with multiple functions which facilitate remote control of the camera 681. The software application and the camera 681 may be configured to communicate via any of the standard wire or wireless communication techniques available. The wireless communication technology may include but is not limited to Bluetooth, WIFI, NFC, etc. In some embodiments, communication between the camera and the electronic device with the software application may be through wired communication. The software application may further be configured to control the camera through the IMI of the electronic device to implement camera functions such as zooming in or out for optimum visibility of the foot. The software application may further be configured to control flash light, store audio visuals and store data in the local memory of the device as well as transmit captured still and/or video images to a remote location such as a cloud storage or remote storage location. Further, the software application may include an option to implement live audio/video broadcasting to remote display/control devices which may be viewed by a healthcare service provider.

Figure 16:
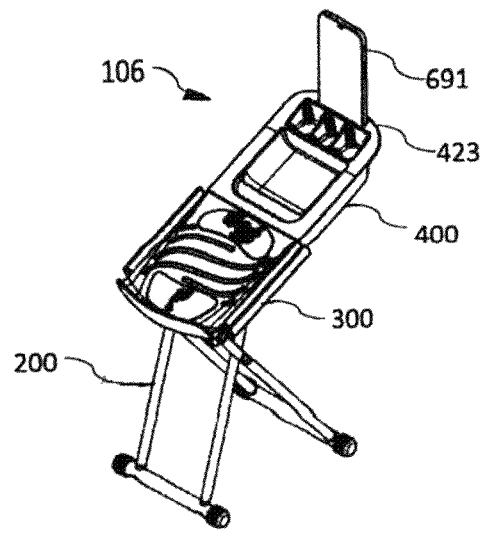
FIG. 16 is a perspective view of another illustrative embodiment of the foot care apparatus with a camera in the form of a smartphone supported by the tray of the apparatus.
Figure 17:
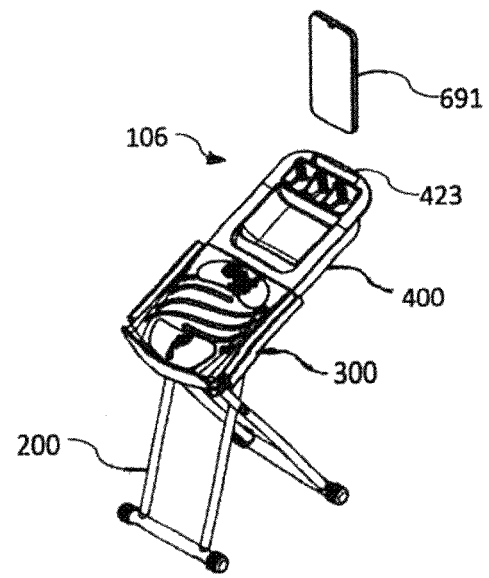
FIG. 17 is an exploded perspective view of the illustrative foot care apparatus with smartphone illustrated in FIG. 16.

Referring next to FIGS. 16 and 17 of the drawings, a smartphone 691 may be provided in the holder slot 423 of the foot care apparatus 106. The smartphone 691 may include but is not limited to a smart mobile phone or a tablet. The smartphone 691 may include a built-in camera with flash light having capability to capture still and/or video images of the foot. The smartphone 691 may be powered up by connecting to the battery bank 520 typically via a USB or other port or compatible connector.

In some embodiments, the smartphone 691 may be provided with a software application having built in artificial intelligence to capture the still and/or video images of the foot as well as store internally, analyze and identify the possible disease or infections in the foot and alert the patient or the health service provider along with the report by mobile communication.

Figure 18:
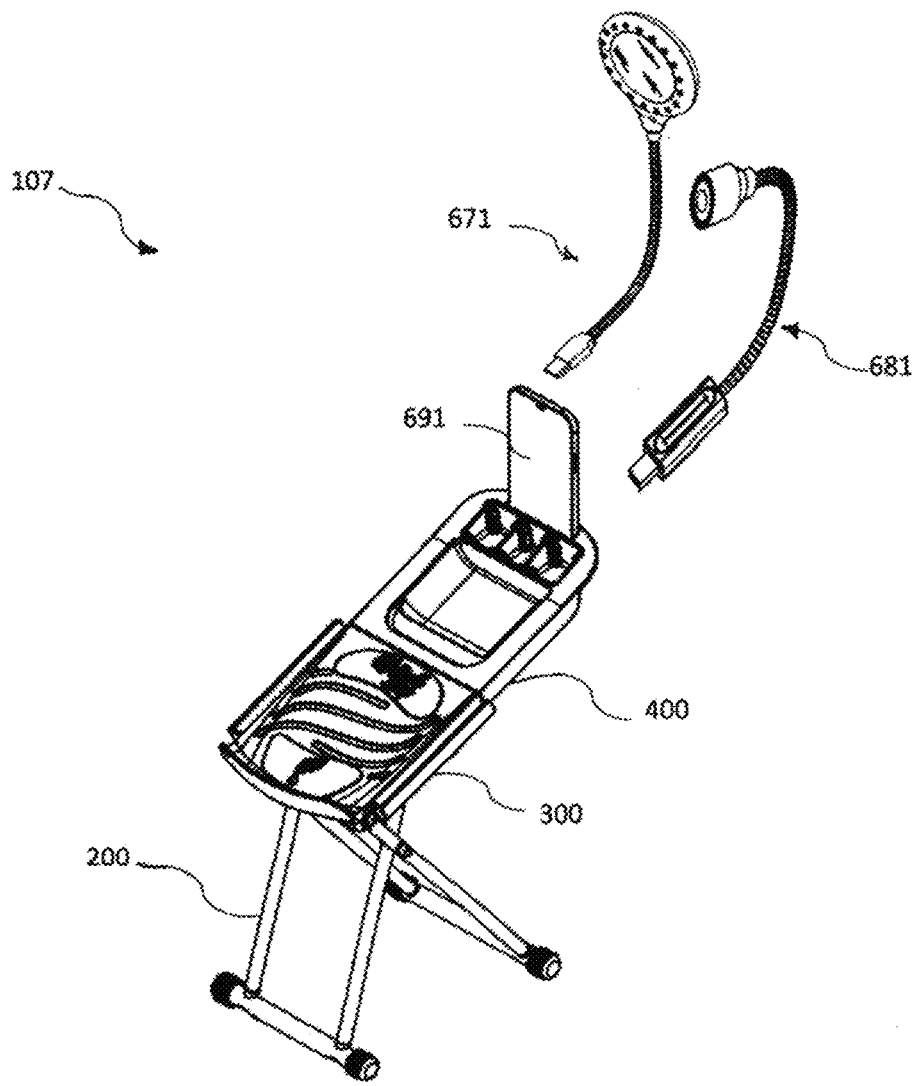
FIG. 18 is an exploded perspective view of another illustrative embodiment of the foot care apparatus with a combination of a mirror and magnifying lens/light assembly, smart digital camera and smartphone.

Referring next to FIG. 18 of the drawings, in some embodiments, the foot care apparatus 107 can be provided with the mirror or magnifying lens/light assembly 671, camera 681 and smart phone 691. In the non-limiting example illustrated in FIG. 18, the foot care apparatus 107 is provided without the mirror (601, 602, 603) and the storage box 510, but with the mirror or magnifying lens/light assembly 671, the camera 681 and smart phone 691. The lights of the mirror or magnifying lens/light assembly 671 can be used along with camera 681 as well as with smart phone 691, such that the camera or the smart phone can take a high quality picture/video with light focused on the part of interest on the foot or also with a combination of the camera or smart phone built in flash light and the lights from the assembly 671.

In some embodiments, by placing a foot over the mirror 601,602,603 of the foot care apparatus 101 through 105, either with or without the storage box 520, a patient can bend or move the foot as required to view the refection of the portions of the foot which are otherwise difficult to view on the mirror 601, 602, 603.

In some embodiments, by placing a foot over the mirror 601, 602, 603 of the foot care apparatus 101 through 103, or directly on the footrest 300 without the mirror 601, 602, 603 of the foot care apparatus 104, with the camera 671 connected to the battery back 520 and controlled by the software application, can place the foot as required over the footrest 300 to capture still and/or video images of the foot. The images of the foot may be transmitted to a doctor or other healthcare service provider.

Referring next to FIGS. 19-27 of the drawings, an illustrative embodiment of an image capturing foot care apparatus 108 and a camera mounting device 700 therefor is illustrated. The foot care apparatus 108 may have a design which is the same as or similar to any of the foot care apparatuses 100-107 heretofore described with respect to FIGS. 1-18. Accordingly, the descriptions of the foot care apparatuses 100-107 set forth herein above are incorporated by reference herein in their entireties with respect to the foot care apparatus 108.

The camera mounting device 700 may include a camera positioning rail 701. A rail mount assembly 710 may be provided on the camera positioning rail 701. The rail mount assembly 710 may facilitate attachment of the camera positioning rail 701 to the tray 400 of the foot care apparatus 108, typically as will be hereinafter described.

Figure 19:
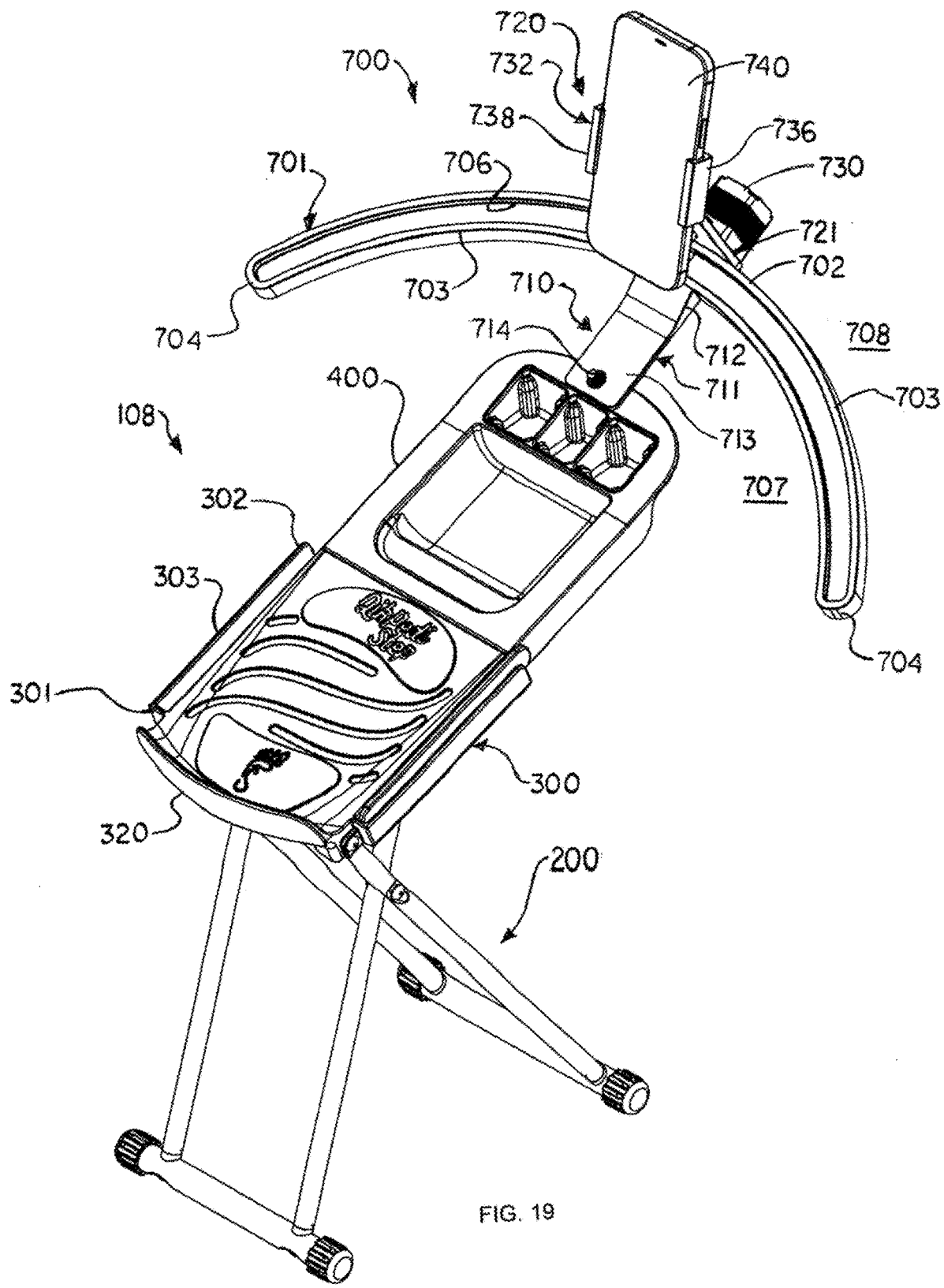
FIG. 19 is a front perspective view of an illustrative embodiment of an image capturing foot care apparatus and camera mounting device therefor, with a smartphone mounted on the camera mounting device and oriented in a portrait orientation.
Figure 21:
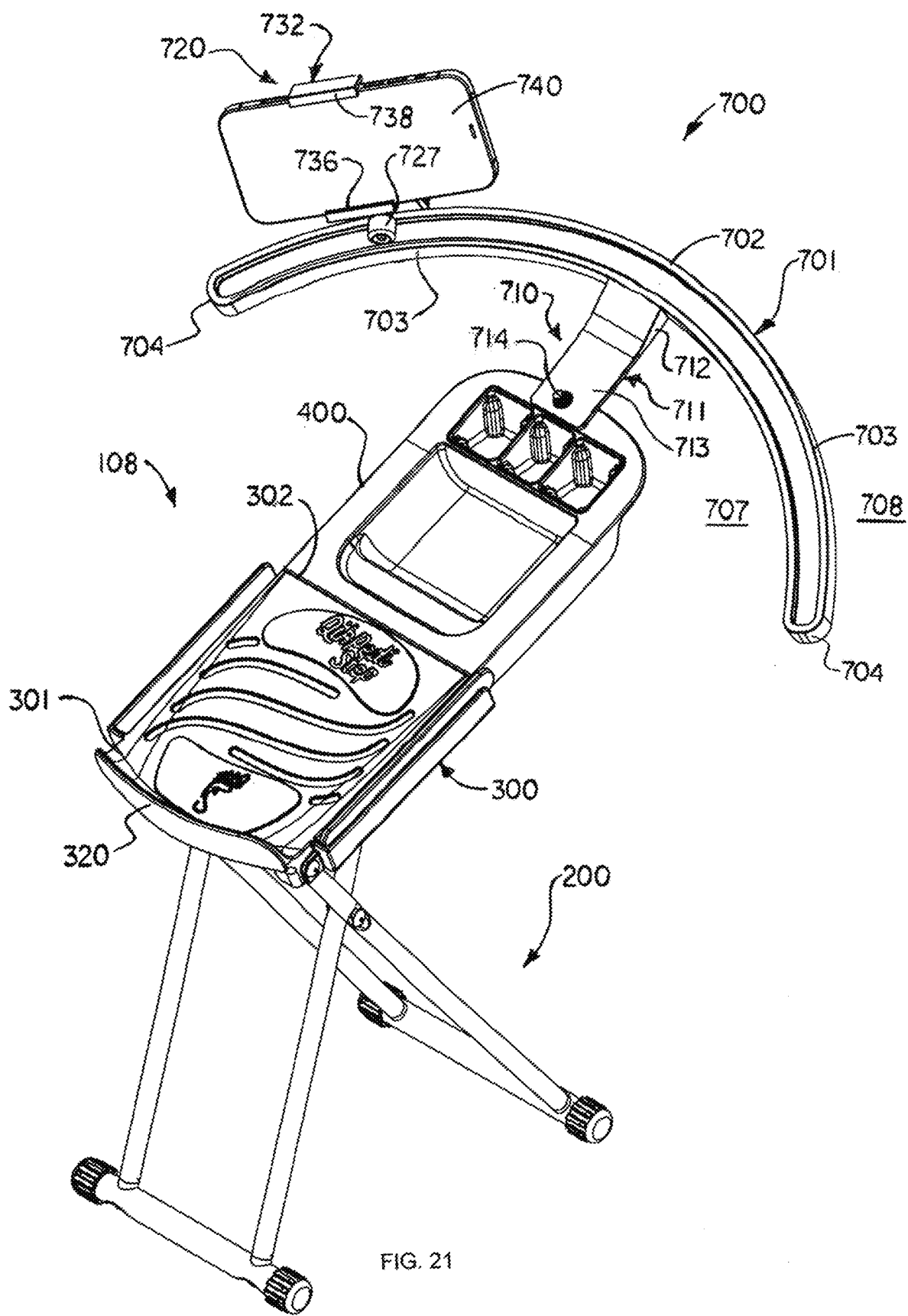
FIG. 21 is a front perspective view of the apparatus and device illustrated in FIG. 19, with the smartphone oriented in a landscape orientation.
Figure 22:
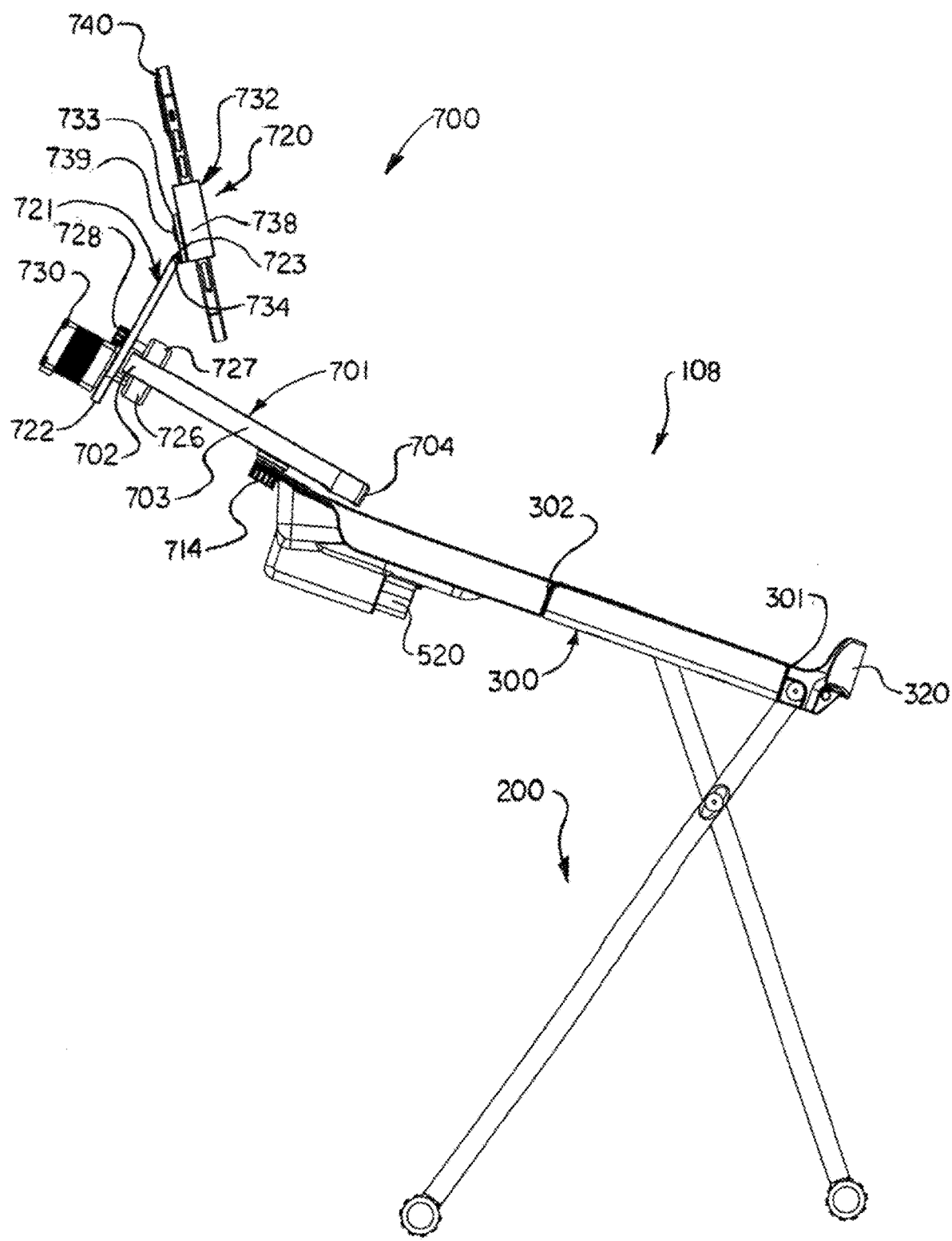
FIG. 22 is a right-side view of the illustrative apparatus and device therefore illustrated in FIG. 19.
Figure 23:
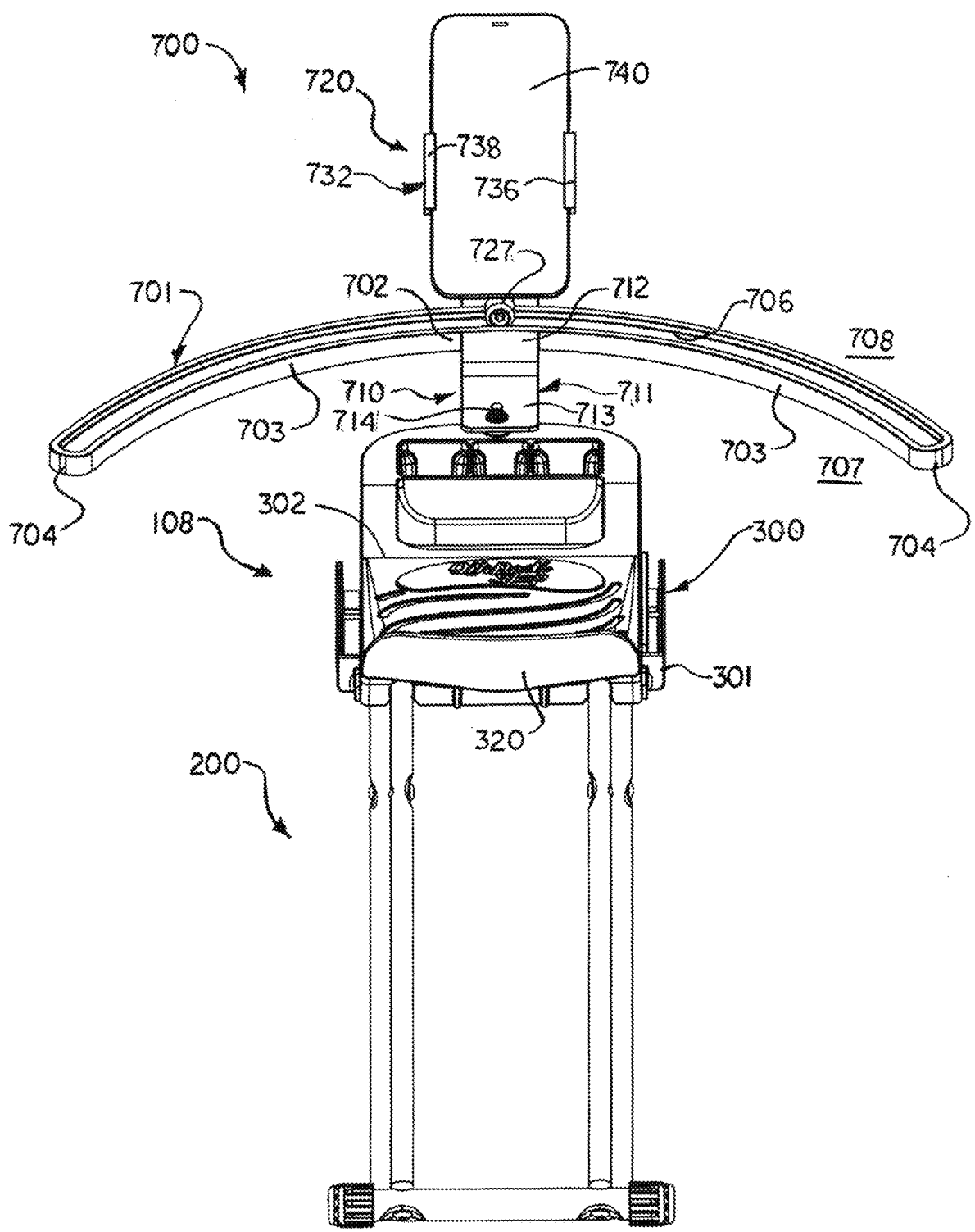
FIG. 23 is a rear view of the illustrative apparatus and device illustrated in FIG. 19.
Figure 24:
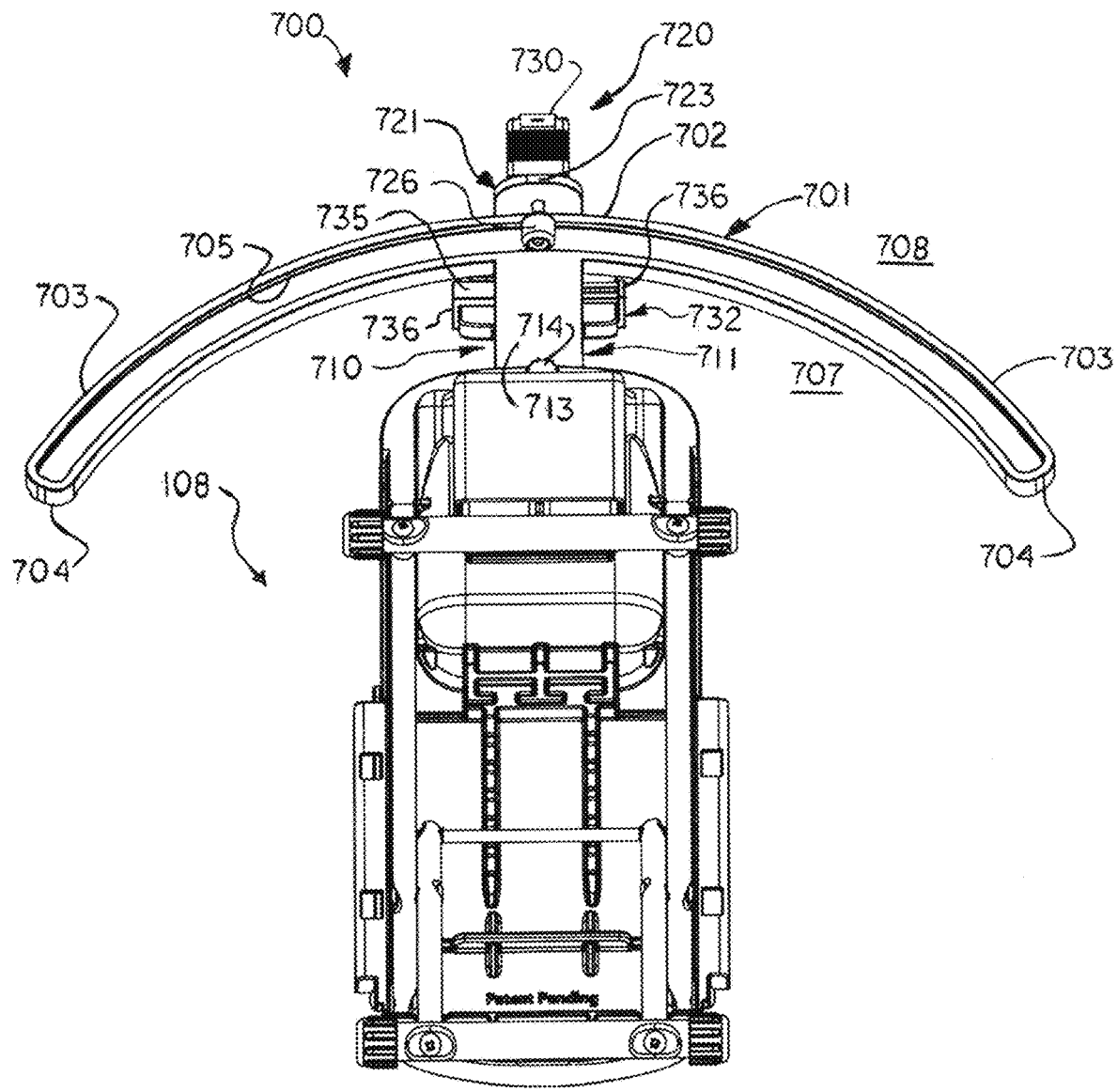
FIG. 24 is a bottom view of the illustrative apparatus and device illustrated in FIG. 19.

A camera carriage 720 may be configured to traverse the camera positioning rail 701. The camera carriage 720 may be configured to support a smartphone 740 or other electronic device having a camera. Accordingly, the smartphone 740 may be suitably positioned to capture still and/or video images of a foot (not illustrated) of a patient or user as the user rests the foot on the footrest 300 of the foot care apparatus 108, typically with the bottom or sole of the foot facing the camera in the smartphone 740. The camera carriage 720 may be positioned at any selected position or location along the length of the camera positioning rail 701 to capture images of any portion of the bottom or sole of the foot. As will be hereinafter further described, the camera carriage 720 may be configured to support the smartphone 740 in a portrait orientation, as illustrated in FIG. 19; a landscape orientation, as illustrated in FIG. 21; or at any other orientation between the portrait orientation and the landscape orientation, according to the viewing and imaging requirements of the user.

The camera positioning rail 701 of the camera mount device 700 may be elongated with a center rail portion 702 and a pair of side rail portions 703 which extend from the center rail portion 702. In some embodiments, the camera positioning rail 701 may be curved or arcuate with a concave rail side 707 and a convex rail side 708. A pair of rail ends 704 may terminate the respective side rail portions 703 of the camera positioning rail 701. The camera positioning rail 701 may have at least one rail groove 705, 706. Accordingly, the camera carriage 720 may be configured to engage the rail groove or grooves 705, 706 as the camera carriage 720 traverses the camera positioning rail 701, typically as will be hereinafter described. The rail groove or grooves 705, 706 may be coextensive with the center rail portion 702 and the side rail portions 703, typically extending from one rail end 704 to the other rail end 704 of the camera positioning rail 701. In some embodiments, the camera positioning rail 701 may have a lower rail groove 705 (FIG. 24) and an upper rail groove 706.

The rail mount assembly 710 of the camera mount device 700 may have any design which is suitable to mount the camera positioning rail 701 on the tray 400 of the foot care apparatus 108. Accordingly, in some embodiments, the rail mount assembly 710 may include a rail mount bracket 711. The rail mount bracket 711 may be elongated with a rail attachment portion 712 and a fastening portion 713 which extends from the rail attachment portion 712. The center rail portion 702 of the camera positioning rail 701 may be attached to the rail attachment portion 712 of the rail mount bracket 711 according to the knowledge of those skilled in the art, with the concave rail side 707 of the camera positioning rail 701 typically facing the foot care apparatus 108. Accordingly, in some embodiments, the center rail portion 702 may be attached to the rail attachment portion 712 using screws, bolts, brackets, clamps and/or other suitable attachment fasteners or mechanisms (not illustrated) known by those skilled in the art. In some embodiments, the center rail portion 702 may be fabricated in one piece with the rail attachment portion 712 according to the knowledge of those skilled in the art.

The fastening portion 713 of the rail mount assembly 710 may be attached to the tray 400 of the foot care apparatus 108 using any technique which is suitable for the purpose. Accordingly, in some embodiments, at least one device mount bracket fastener 714 may be extended through fastener openings (not illustrated) in the respective fastening portion 713 and tray 400. A securing nut (not illustrated) may be threaded and tightened on the device mount bracket fastener 714. In some embodiments, a clamp, bracket or the like (not illustrated) may be provided on the fastening portion 713 of the rail mount bracket 711. The clamp, bracket or other mechanism may be suitably configured to detachably engage the tray 400 to facilitate mounting of the camera positioning rail 701 on the tray 400.

In some embodiments, the camera positioning rail 701 may be selectively positionally adjustable with respect to the tray 400 along a fore/aft axis. This capability may facilitate selective capturing of close or far images of the patient's foot using the camera in the smartphone 740. Accordingly, the rail attachment portion 712 may be telescopically extendable and retractable with respect to the fastening portion 713 of the rail mount bracket 711. Additionally or alternatively, an elongated bracket adjustment slot (not illustrated) may extend through the fastening portion 713. The device mount bracket fastener 714 may extend through the bracket adjustment slot. Accordingly, the rail mount bracket 711 may be selectively extendable and retractable with respect to the tray 400 as the rail attachment portion 712 extends and retracts with respect to the fastening portion 713 and the device mount bracket fastener 714 traverses the bracket adjustment slot.

Figure 27:
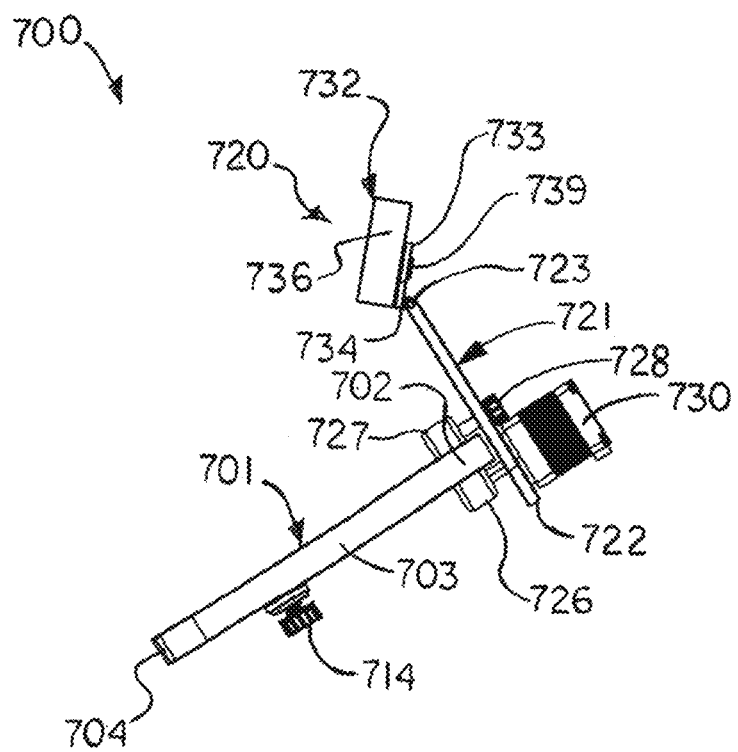
FIG. 27 is a left view of the illustrative camera mounting device illustrated in FIG. 25.

The camera carriage 720 may have any design which is suitable for the purpose of supporting the smartphone 740 with the camera of the smartphone 740 facing the bottom or sole of the patient's foot and configured to traverse the camera positioning rail 701. Accordingly, as particularly illustrated in FIGS. 25-27, in some embodiments, the camera carriage 720 may have a carriage mount bracket 721. As illustrated in FIG. 27, the carriage mount bracket 721 may be elongated with a lower bracket end 722 and an upper bracket end 723. At least one carriage wheel 726, 727 may extend from the carriage support bracket 721, typically proximate the lower bracket end 722. The carriage wheel 726, 727 may be configured to engage at least one of the rail grooves 705, 706 in the camera positioning rail 701. For example and without limitation, in some embodiments, a lower carriage wheel 726 and an upper carriage wheel 727 may extend from the carriage support bracket 721 in vertically spaced-apart relationship to each other. The lower carriage wheel 726 may engage the lower rail groove 705, and the upper carriage wheel 727 may engage the upper rail groove 706 in the camera positioning rail 701. Accordingly, the lower carriage wheel 726 and the upper carriage wheel 727 may stabilize the camera carriage 720 as the camera carriage 720 traverses the camera positioning rail 701.

In some embodiments, a carriage drive device 730 may drivingly engage at least one of the lower carriage wheel 726 and the upper carriage wheel 727 for rotation. The carriage drive device 730 may include any type of device or mechanism which is suitable for the purpose. For example and without limitation, in some embodiments, the carriage drive device 730 may include an electric motor. In some embodiments, the carriage drive device 730 may include a manually actuatable handle. The carriage drive device 730 may directly engage the lower carriage wheel 726 for rotation. The upper carriage wheel 727 may be attached to the carriage support bracket 721 via a wheel fastener 728. The carriage drive device 730 may include a manually operated switch (not illustrated) and/or may be operable wirelessly or remotely according to the knowledge of those skilled in the art.

Figure 25:
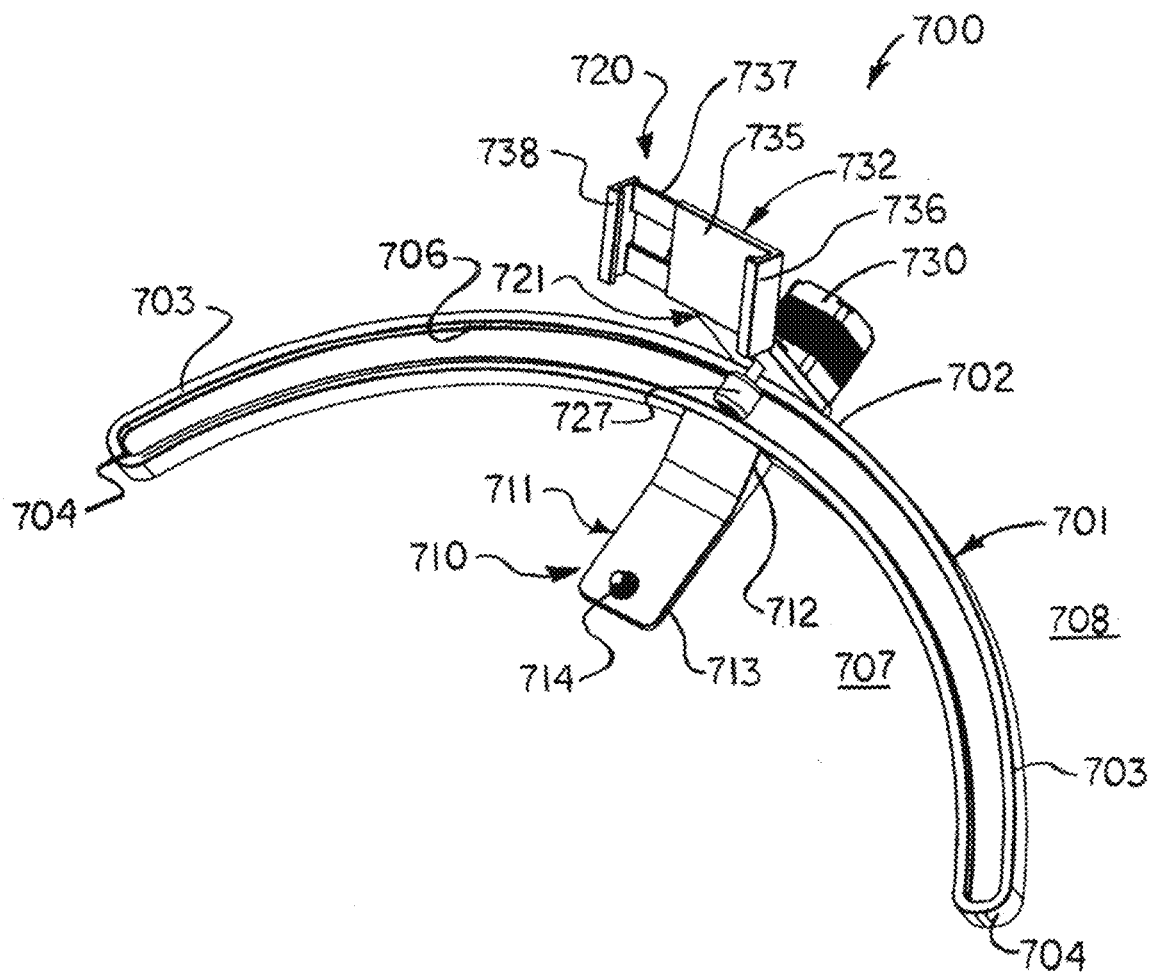
FIG. 25 is a front perspective view of the illustrative camera mounting device, removed from the foot care apparatus illustrated in FIG. 19, with the smartphone removed from the camera mount device.
Figure 26:
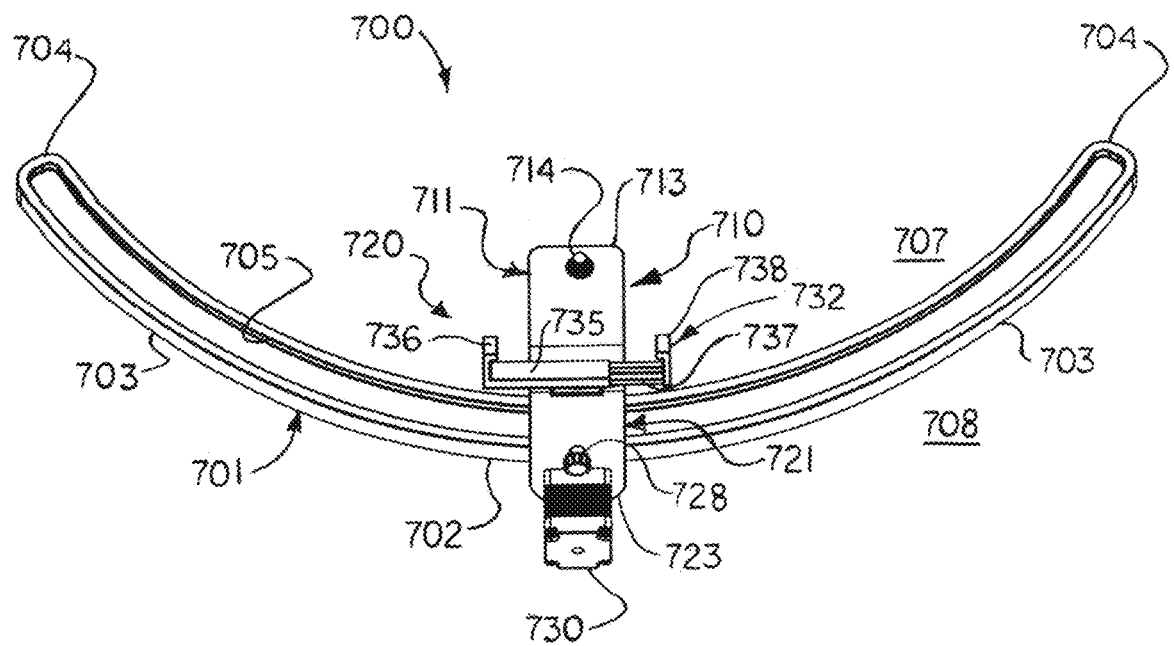
FIG. 26 is a top view of the illustrative camera mounting device illustrated in FIG. 25.

A camera mount bracket 732 may be supported by the carriage support bracket 721. The camera mount bracket 732 may have any design which is suitable to support the smartphone 740. Accordingly, as illustrated in FIG. 25, in some embodiments, the camera mount bracket 732 may include a base bracket portion 735 having a base bracket portion flange 736. The base bracket portion 735 may be fixed relative to the carriage support bracket 721. An adjustable bracket portion 737 may be selectively extendable and retractable relative to the base bracket portion 735. The adjustable bracket portion 737 may have an adjustable bracket portion flange 738 which is spaced-apart relative to the base bracket portion flange 736 of the base bracket portion 735. Accordingly, by extending the adjustable bracket portion 737 relative to the base bracket portion 735, the camera mount bracket 732 may be sized and configured to receive and securely hold the smartphone 740 between the base bracket portion flange 736 and the adjustable bracket portion flange 738.

As illustrated in FIG. 27, in some embodiments, the camera mount bracket 732 may be pivotally attached to the carriage support bracket 721 and movable within a forward-rearward vertical plane. Accordingly, a bracket mount plate 733 may be pivotally attached to the upper bracket end 723 of the carriage support bracket 721 via a bracket pivot pin 734. The base bracket portion 735 of the camera mount bracket 732 may be attached to the bracket mount plate 733. The camera mount bracket 732 may thus be selectively pivoted forwardly and rearwardly about the bracket pivot pin 734 to selectively angle the smartphone 740 forwards, backwards or straight within a vertical fore-aft plane.

In some embodiments, the camera mount bracket 732 may be rotatably mounted with respect to the camera support bracket 721. Accordingly, a camera mount bracket fastener 739 may pivotally attach the base bracket portion 735 of the camera mount bracket 732 to the bracket mount plate 733. The camera mount bracket 732 may thus be pivoted about the camera mount bracket fastener 739 to deploy the smartphone 740 in the portrait orientation (FIG. 19), the landscape orientation (FIG. 21) or other orientation depending on the viewing and imaging requirements of the user's foot.

Figure 20:
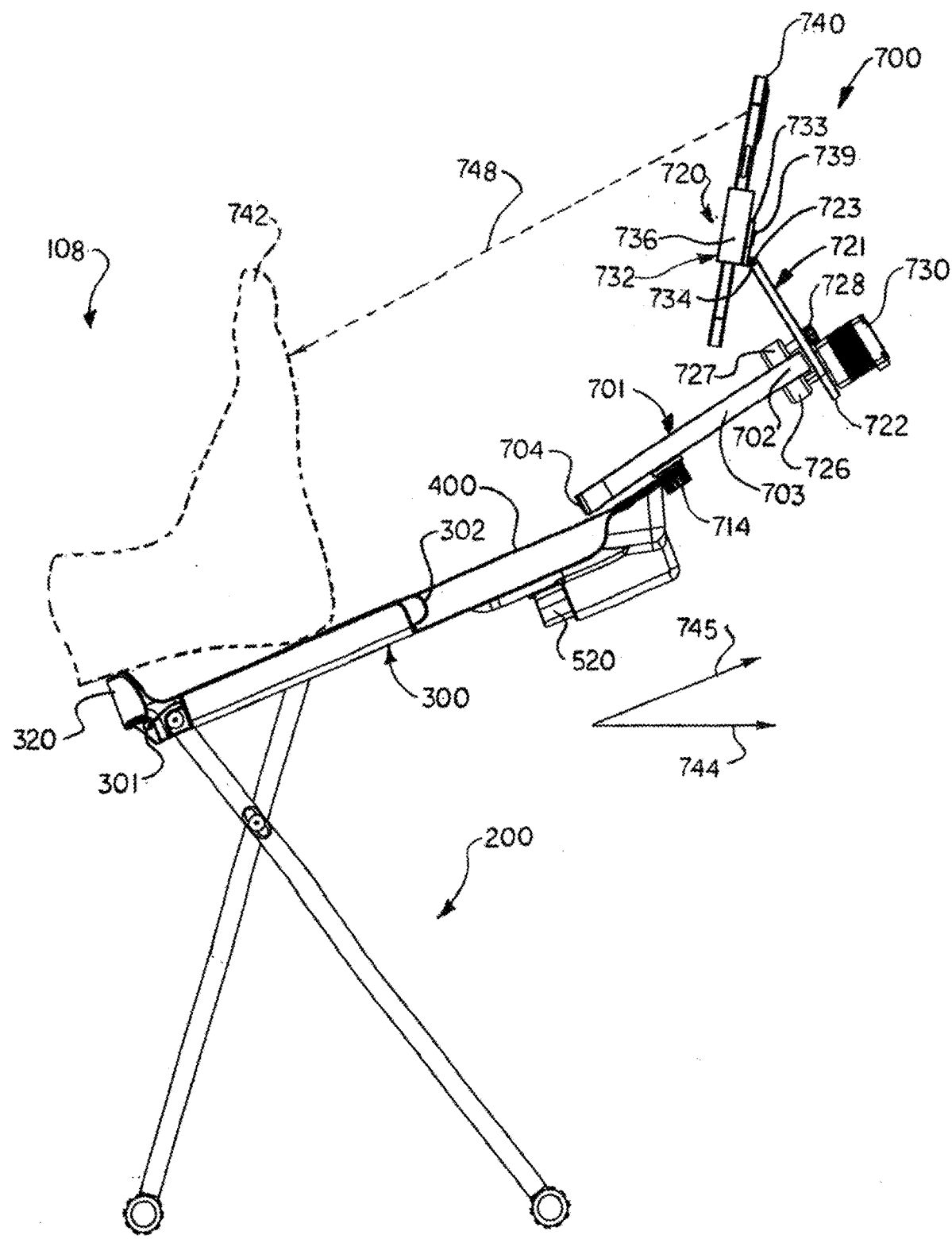
FIG. 20 is a left side view of the image capturing foot care apparatus and camera mounting device therefore illustrated in FIG. 19.

As particularly illustrated in FIG. 20, the footrest 300 and the tray 400 of the foot care apparatus 108 and the camera positioning rail 701 of the camera mount device 700 may be disposed within an imaging plane 745. The support stand 200 may be adjusted such that the imaging plane 745 coincides with a horizontal plane 744 or slopes with respect to the horizontal plane 744 upwardly from the heel rest 320 of the footrest 300 to the camera mount device 700, as illustrated. Therefore, the camera mount device 700 may be disposed higher than the footrest 300. Accordingly, as it rests on the footrest 300, the foot 742 of the user may be oriented upwardly towards the smartphone 740, while the camera in the smartphone 740 faces downwardly toward the user's foot 742. The imaging line 748 may thus slope downwardly from the smartphone 740 to the user's foot 742. Alternatively, the support stand 200 may be adjusted such that the imaging line 748 is horizontal from the smartphone 740 to the user's foot 742.

In typical application of the foot care apparatus 108, the smartphone 740 may be placed in the camera mount bracket 732 of the camera carriage 720 typically by securing the smartphone 740 between the base bracket portion flange 736 of the base bracket portion 735 and the adjustable bracket portion flange 738 of the adjustable bracket portion 737. The smartphone 740 may be selectively oriented in the portrait orientation (FIG. 19), the landscape orientation (FIG. 21) or other orientation typically by pivoting or rotating the camera mount bracket 732 about the camera mount bracket fastener 739. The smartphone 740 may be tilted forwardly or rearwardly typically by pivoting the camera mount bracket 732 about the bracket pivot pin 734 (FIG. 27). The position of the camera carriage 720 and the smartphone 740 along the camera positioning rail 701 may be selected typically by operation of the carriage drive device 730.

A patient or user (not illustrated) may place a foot on the footrest 300 of the foot care apparatus 108 with the heel of the foot typically resting on the heel rest 320 of the footrest 300. The smartphone 740 may be operated to capture still and/or video images of the bottom of the foot and may be operated to transmit the images to healthcare personnel.

Referring next to FIGS. 28-35 of the drawings, an alternative illustrative embodiment of an image capturing foot care apparatus 109 and camera mounting device 800 therefor is illustrated. The foot care apparatus 109 may have a design which is the same as or similar to any of the foot care apparatuses 100-107 heretofore described with respect to FIGS. 1-18. Accordingly, the descriptions of the foot care apparatuses 100-107 set forth herein above are incorporated by reference herein in their entireties with respect to the foot care apparatus 109.

Figure 28:
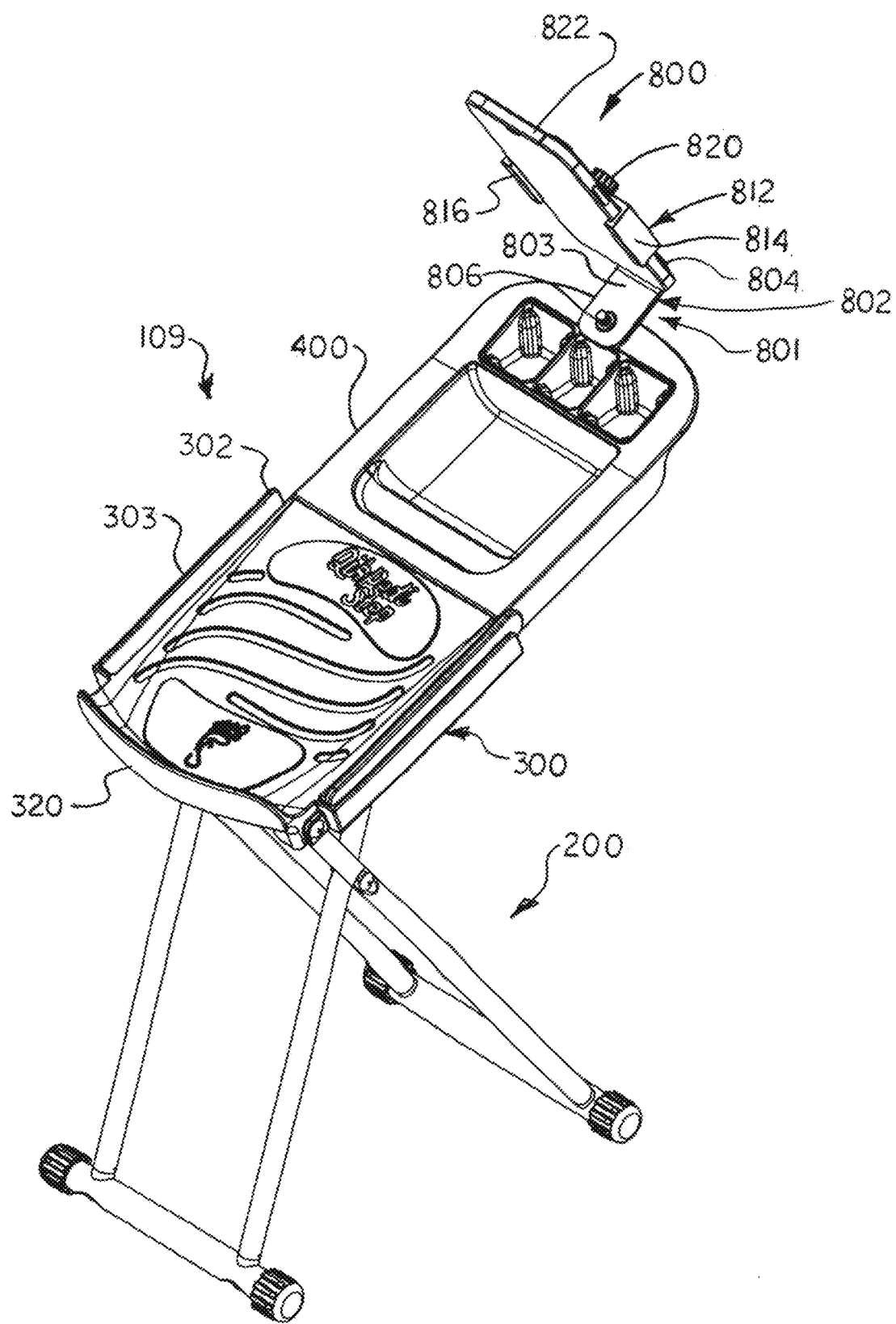
FIG. 28 is a front perspective view of an alternative illustrative embodiment of an image capturing foot care apparatus and camera mounting device therefor, with a smartphone mounted on the camera mount device and oriented in a portrait orientation.
Figure 30:
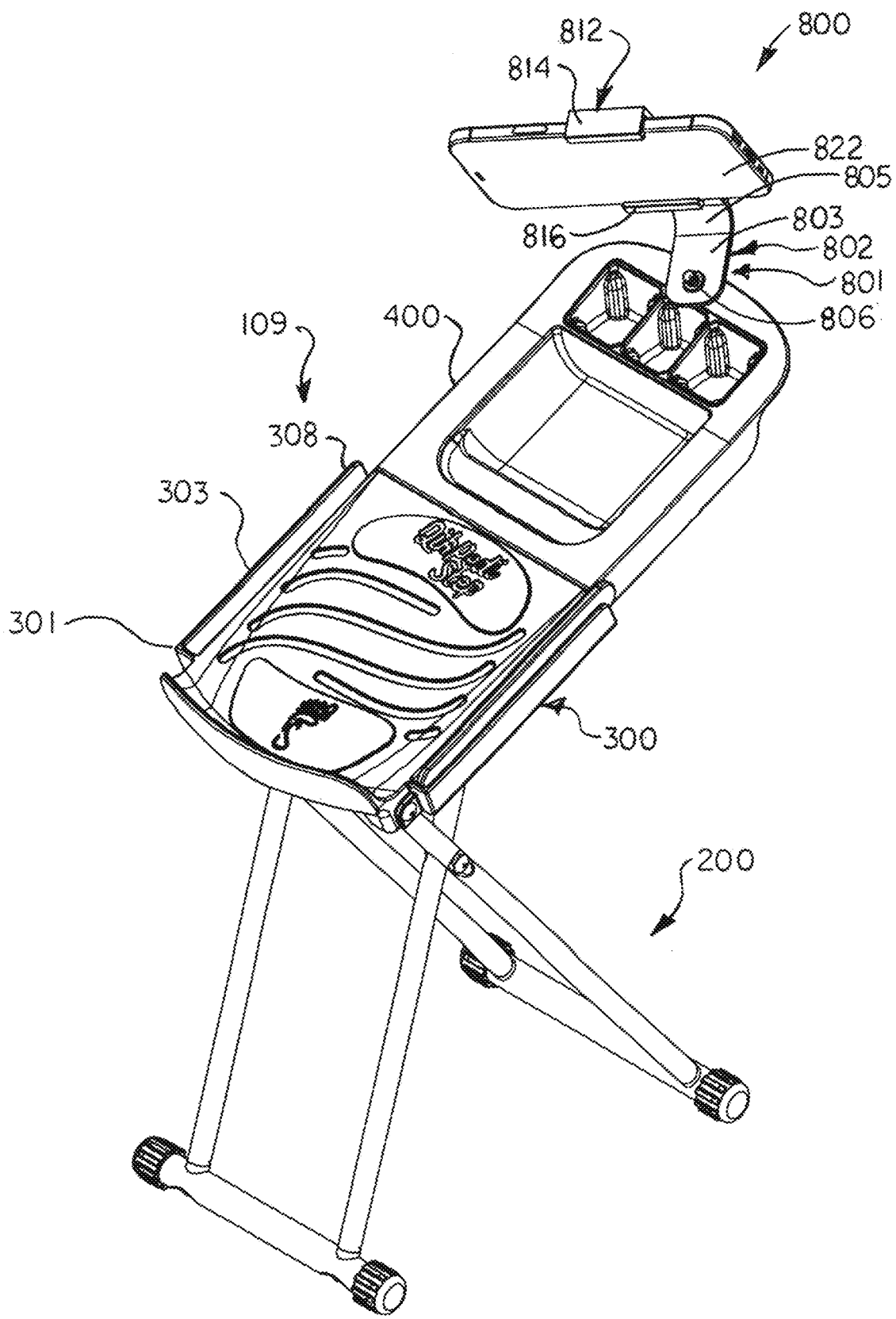
FIG. 30 is a front perspective view of the illustrative apparatus and device illustrated in FIG. 28, with the smartphone oriented in a landscape orientation.
Figure 31:
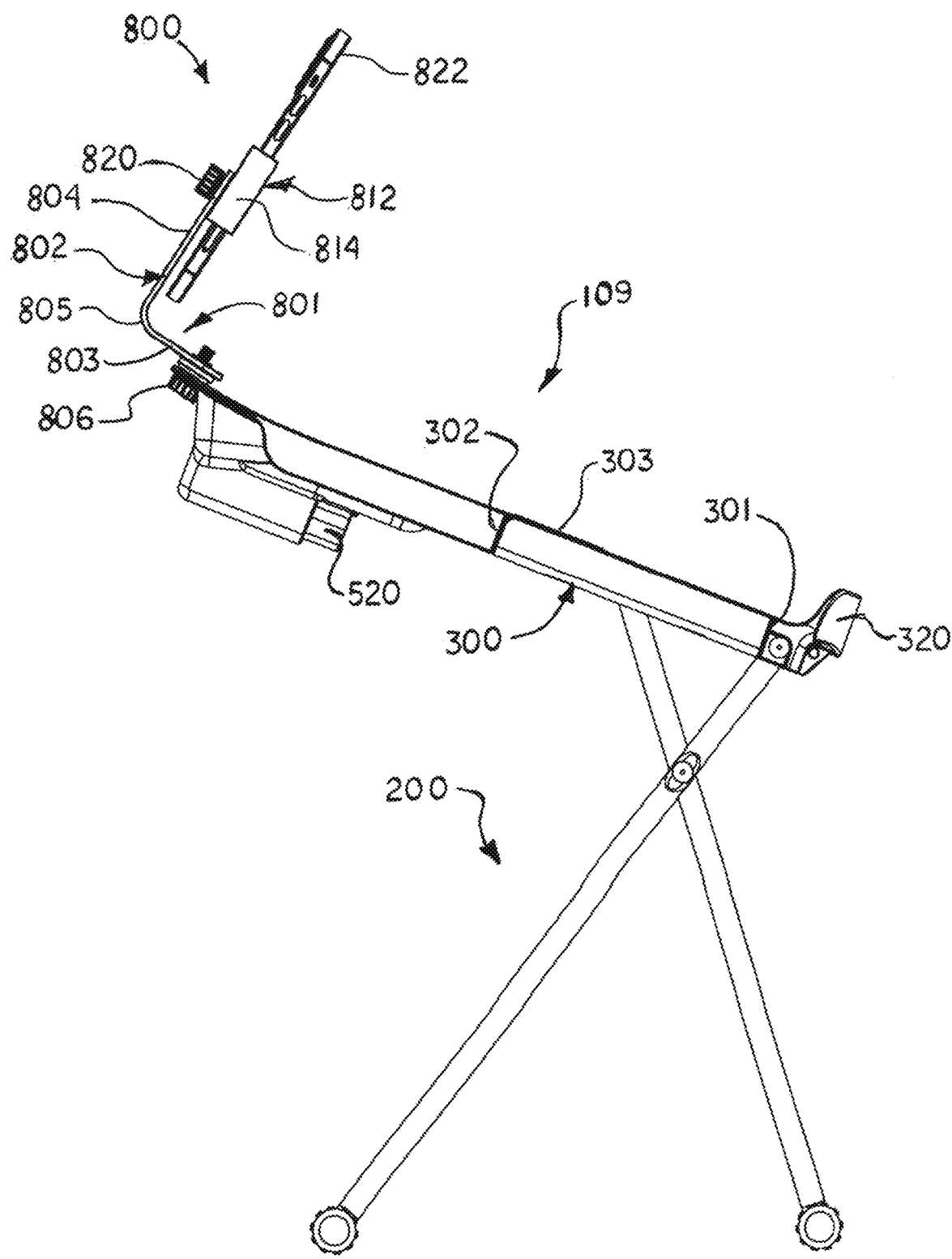
FIG. 31 is a right view of the illustrative apparatus and device illustrated in FIG. 25.
Figure 32:
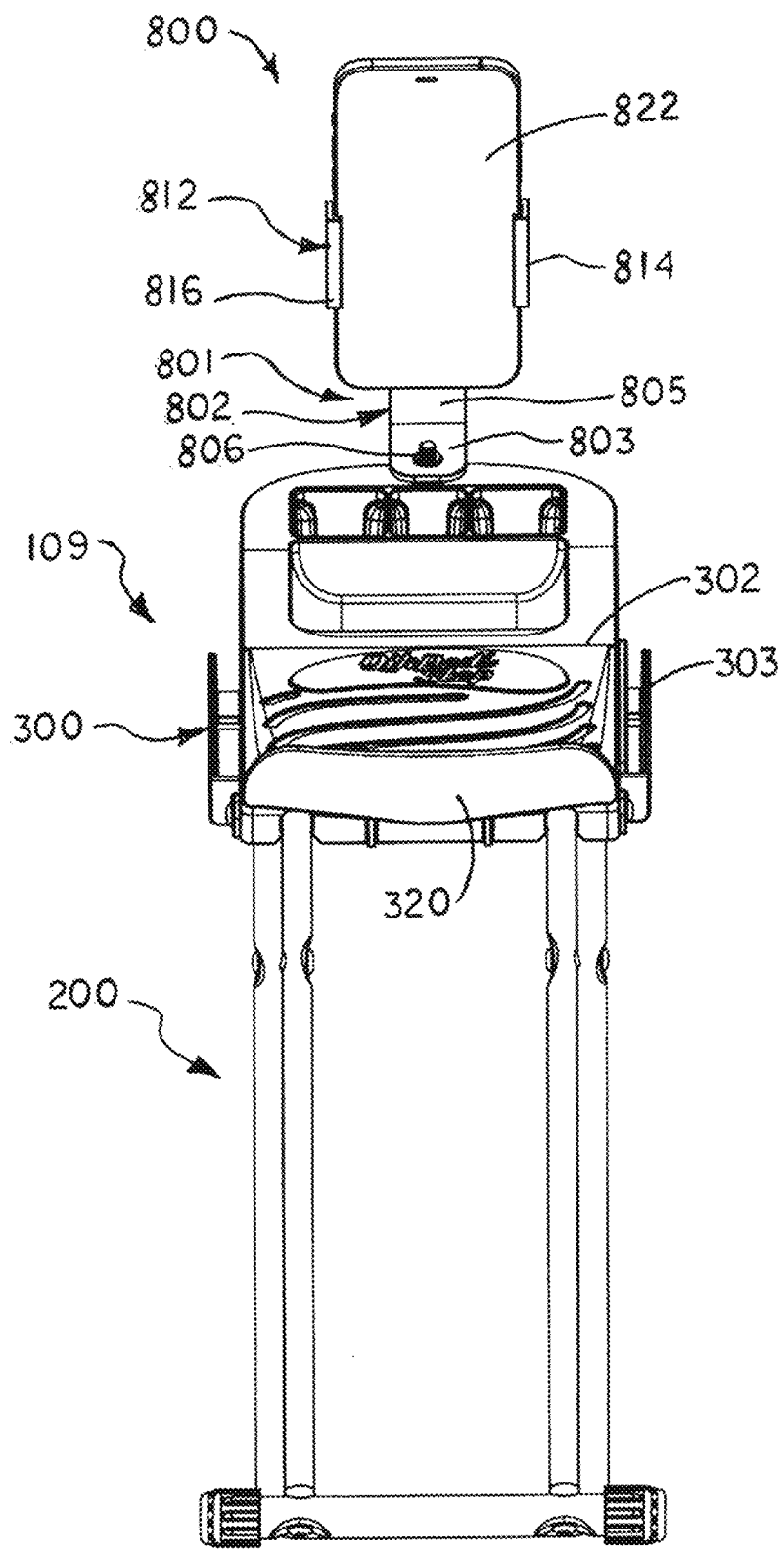
FIG. 32 is a rear view of the illustrative apparatus and device illustrated in FIG. 25.
Figure 33:
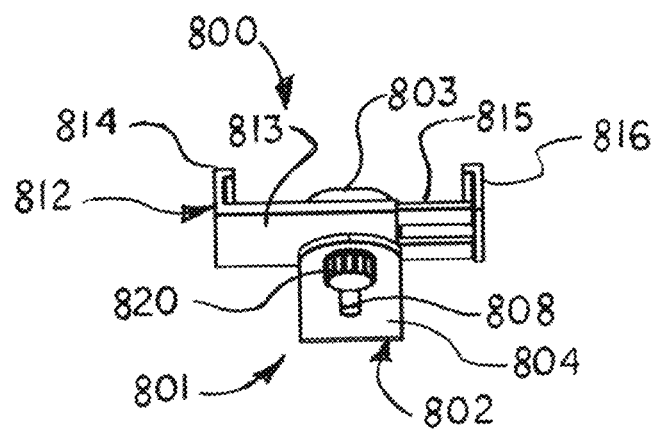
FIG. 33 is a top view of the illustrative camera mounting device, removed from the foot care apparatus illustrated in FIG. 25.
Figure 34:
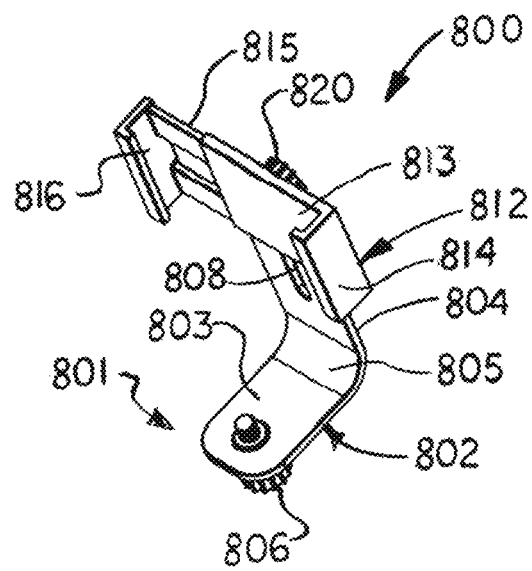
FIG. 34 is a top front perspective view of the illustrative camera mounting device illustrated in FIG. 33.
Figure 35:
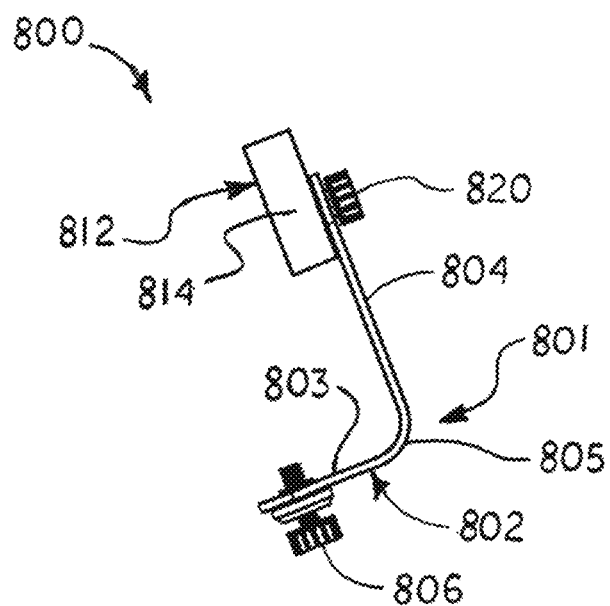
FIG. 35 is a left view of the illustrative camera mounting device illustrated in FIG. 33.

The camera mounting device 800 may include a device mount assembly 801. A camera mount bracket 812 may be supported by the device mount assembly 801. The camera mount bracket 812 may be configured to support a smartphone 822 or other electronic device having a camera. Accordingly, the smartphone 822 may be suitably positioned to capture still and/or video images of the foot (not illustrated) of the patient or user as the user rests the foot on the footrest of the foot care apparatus 109, typically with the bottom or sole of the foot facing the camera in the smartphone 822. The camera mount bracket 812 may be positioned at any of multiple angles with respect to the tray 400 to capture images of any portion of the bottom or sole of the foot. The camera mount bracket 812 may be configured to support the smartphone 822 in a portrait orientation, as illustrated in FIG. 28; a landscape orientation, as illustrated in FIG. 30; or any other orientation between the portrait orientation and the landscape orientation according to the viewing and imaging requirements of the user.

The device mount assembly 801 may include an assembly mount bracket 802. The camera mount bracket 812 may be supported by the assembly mount bracket 802. The assembly mount bracket 802 may have a base bracket portion 803 and a camera support portion 804. A connecting portion 805 may connect the camera support portion 804 to the base bracket portion 803. The camera support portion 804 may be oriented in perpendicular relationship to the base bracket portion 803 of the assembly mount bracket 802.

The base bracket portion 803 of the assembly mount bracket 802 may be configured for attachment to the tray 400 of the foot care apparatus 109 using any technique which is suitable for the purpose. Accordingly, in some embodiments, a camera angle adjustment knob 806 may extend through registering knob openings (not illustrated) in the tray 400 and the base bracket portion 803, respectively. The camera angle adjustment knob 806 may be loosened to facilitate side-to-side angular adjustment of the camera mount device 800 and the smartphone 822 held therein with respect to the tray 400. The camera angle adjustment knob 806 may be tightened to secure the camera mount device 800 at the selected angular position.

In some embodiments, an elongated bracket adjustment slot (not illustrated) may be provided in the tray 400 and/or in the base bracket portion 803. The camera angle adjustment knob 806 may extend through the bracket adjustment slot to facilitate forward/rearward adjustment of the camera mount device 800 and smartphone 822 with respect to the foot care apparatus 109.

The camera mount bracket 812 may have any design which is suitable for securely holding the smartphone 822. Accordingly, in some embodiments, the camera mount bracket 812 may include a base bracket portion 813. The base bracket portion 813 of the camera mount bracket 812 may be attached to the camera support portion 804 of the assembly mount bracket 802 typically as will be hereinafter described. A base bracket flange 814 may extend from the base bracket portion 813. An adjustable bracket portion 815 may be selectively extendable and retractable with respect to the base bracket portion 813. An adjustable bracket portion flange 816 may extend from the adjustable bracket portion 815. Accordingly, the adjustable bracket portion 815 can be selectively extended and retracted with respect to the base bracket portion 813 to vary the distance between the base bracket flange 814 and facilitate securement of the smartphone 822 in the camera mount bracket 812.

In some embodiments, the camera mount bracket 813 may be adjustably mounted on the camera support portion 804 of the assembly mount bracket 802. Accordingly, an elongated camera adjustment slot 808 may extend through the camera support portion 804. A threaded bracket adjustment knob 820 may extend through the camera adjustment slot 808 and thread into a knob opening (not illustrated) in the base bracket portion 813. Accordingly, the bracket adjustment knob 820 may be loosened to facilitate vertical adjustment of the camera mount bracket 812 along the camera support portion 804 as the bracket adjustment knob 820 traverses the camera adjustment slot 808. The bracket adjustment knob 820 may be tightened to secure the camera mount bracket 812 at the selected height or position on the camera support portion 804.

Figure 29:
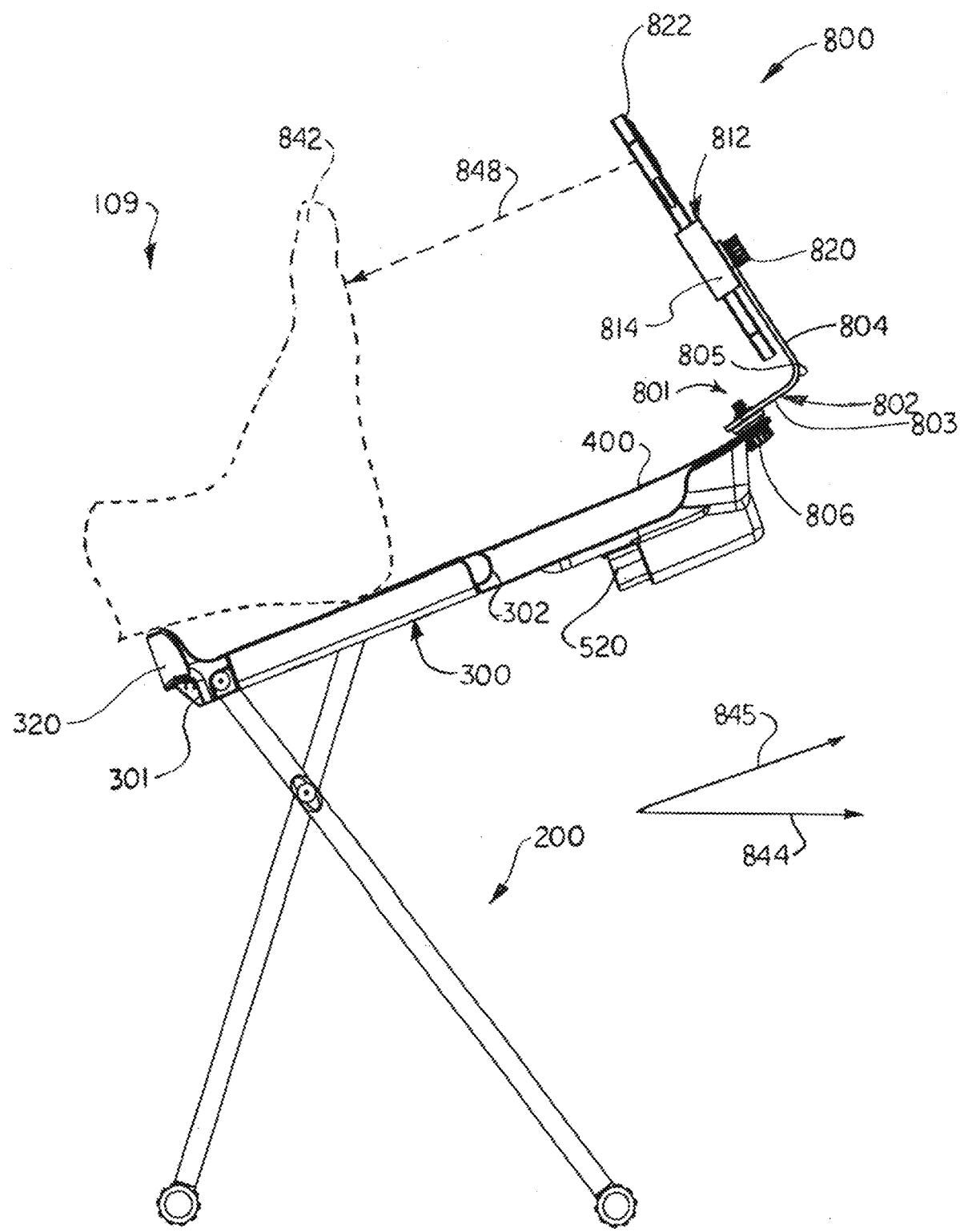
FIG. 29 is a left view of the illustrative apparatus and device illustrated in FIG. 28.

As particularly illustrated in FIG. 29, the footrest 300 and the tray 400 of the foot care apparatus 109 and the base bracket portion 803 on the assembly mount bracket 802 of the device mount assembly 801 of the camera mount device

800 may be disposed within an imaging plane 845. The support stand 200 may be adjusted such that the imaging plane 845 coincides with a horizontal plane 844 or slopes with respect to the horizontal plane 844 upwardly from the heel rest 320 of the footrest 300 to the camera mount device 800, as illustrated. Therefore, the camera mount device 800 may be disposed higher than the footrest 300. Accordingly, as it rests on the footrest 300, the foot 842 of the user may be oriented upwardly towards the smartphone 822, while the camera in the smartphone 822 faces downwardly toward the user's foot 842. The imaging line 848 may thus slope downwardly from the smartphone 822 to the user's foot 842. Alternatively, the support stand 200 may be adjusted such that the imaging line 848 is horizontal from the smartphone 822 to the user's foot 842.

In typical application of the foot care apparatus 109, the smartphone 822 may be placed in the camera mount bracket 812 of the camera mount device 800 typically by securing the smartphone 822 between the base bracket portion flange 814 of the base bracket portion 813 and the adjustable bracket portion flange 816 of the adjustable bracket portion 815. The smartphone 822 may be selectively oriented in the portrait orientation (FIG. 28), the landscape orientation (FIG. 30) or other orientation typically by pivoting the camera mount bracket 812 about the bracket adjustment knob 820.

A patient or user (not illustrated) may place a foot on the footrest 300 of the foot care apparatus 108 with the heel of the foot typically resting on the heel rest 320 of the footrest 300. The smartphone 740 may be operated to capture still and/or video images of the bottom of the foot and may be operated to transmit the images to healthcare personnel. The camera mount bracket 812 may be positioned at a selected height or vertical position on the camera support portion 804 of the assembly mount bracket 802 typically by loosening and tightening the bracket adjustment knob 820 as was heretofore described. The camera mount device 800 may be deployed at any of multiple angles with respect to the tray 400 to capture images of any portion of the bottom or sole of the foot, typically by loosening and tightening the camera angle adjustment knob 806 as was heretofore described.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

The features described with respect to one embodiment may be applied to other embodiments or combined with or interchanged with the features of other embodiments, as appropriate (e.g., being part of furniture items, such as sofas, chairs, beds, etc., but not limited to these), without departing from the scope of the present invention.

Other embodiments of the invention will be apparent to those skilled in the art from consideration of the specification and practice of the invention disclosed herein. It is intended that the provisional specification and examples be considered as exemplary only. The true scope and spirit of the invention will indicated by the claims in the non-provisional application being filed later.

What is claimed is:

1. A foot care apparatus suitable for imaging foot of a user, comprising:
   a support stand;
   a footrest supported by the support stand, the footrest configured to support the foot of the user;
   a tray extending from the footrest; and
   a camera mount device supported by the tray, the camera mount device configured to hold an electronic device having a camera with the camera facing the footrest, the footrest, the tray and the camera mount device disposed within an imaging plane;
   wherein the support stand is adjustable such that the imaging plane coincides with a horizontal plane or slopes with respect to the horizontal plane upwardly from the footrest to the camera mount device;
   wherein the camera mount device comprises a rail mount assembly supported by the tray, an elongated camera positioning rail supported by the rail mount assembly and a camera carriage supported by and configured to traverse the camera positioning rail, the camera carriage configured to hold the electronic device; and
   at least one rail groove in the camera positioning rail and at least one carriage wheel on the camera carriage, the at least one carriage wheel engaging the at least one rail groove.

2. The foot care apparatus of claim 1 wherein the rail mount assembly comprises an elongated rail mount bracket having a rail attachment portion and a fastening portion extending from the rail attachment portion and configured for attachment to the tray, and wherein the camera positioning rail is supported by the rail attachment portion and further comprising a device mount bracket fastener configured to attach the fastening portion of the rail mount bracket to the tray.

3. The foot care apparatus of claim 1 wherein the camera mount device comprises a device mount assembly supported by the tray and a camera mount bracket supported by the device mount assembly, and the camera mount device is configured to hold the electronic device.

4. The foot care apparatus of claim 3 wherein the device mount assembly comprises an L-shaped assembly mount bracket.

5. The foot care apparatus of claim 4 wherein the assembly mount bracket of the device mount assembly comprises a base bracket portion supported by the tray, a camera support portion and a connecting portion connecting the camera support portion to the base bracket portion, and the camera mount bracket is supported by the camera support portion of the assembly mount bracket.

6. A foot care apparatus suitable for imaging a foot of a user, comprising:
   a support stand;
   a footrest supported by the support stand, the footrest configured to support the foot of the user;
   a tray extending from the footrest; and
   a camera mount device supported by the tray, the camera mount device configured to hold an electronic device having a camera with the camera facing the footrest, the footrest, the tray and the camera mount device disposed within an imaging plane; wherein the support stand is adjustable such that the imaging plane coincides with a horizontal plane or slopes with respect to the horizontal plane upwardly from the footrest to the camera mount device;
   wherein the camera mount device comprises a device mount assembly supported by the tray and a camera mount bracket supported by the device mount assembly, and the camera mount device is configured to hold the electronic device;
   wherein the device mount assembly comprises an L-shaped assembly mount bracket;
   wherein the assembly mount bracket of the device mount assembly comprises a base bracket portion supported by the tray, a camera support portion and a connecting portion connecting the camera support portion to the base bracket portion, and the camera mount bracket is supported by the camera support portion of the assembly mount bracket; and wherein the base bracket portion of the assembly mount bracket is configured for side-to-side angular adjustment with respect to the tray and the camera mount bracket is vertically and rotatably adjustable with respect to the camera support portion of the assembly mount bracket.

7. A foot care apparatus suitable for imaging a foot of a user, comprising:

a support stand;

a footrest supported by the support stand, the footrest configured to support the foot of the user;

a tray extending from the footrest; and a camera mount device comprising:

a device mount assembly supported by the tray; and a camera mount bracket supported by the device mount assembly, the camera mount bracket configured to hold an electronic device having a camera with the camera facing the footrest, the footrest, the tray and the camera mount device disposed within an imaging plane, the camera mount bracket configured to hold the electronic device in a landscape orientation, a portrait orientation and orientations between the landscape orientation and the portrait orientation; and wherein the support stand is adjustable such that the imaging plane coincides with a horizontal plane or slopes with respect to the horizontal plane upwardly from the footrest to the camera mount device;

wherein the device mount assembly comprises an assembly mount bracket having a base bracket portion supported by the tray, a camera support portion and a connecting portion connecting the camera support portion to the base bracket portion, and wherein the camera mount bracket is supported by the camera support portion;

wherein the camera mount bracket is adjustably supported by the camera support portion of the assembly mount bracket; and wherein the camera mount bracket comprises a base bracket portion supported by the camera support portion of the assembly mount bracket, a base bracket portion flange extending from the base bracket portion, an adjustable bracket portion extendable and retractable with respect to the base bracket portion and an adjustable bracket portion flange extending from the adjustable bracket portion.

8. A foot care apparatus suitable for imaging a foot of a user, comprising:

a support stand;

a footrest supported by the support stand, the footrest configured to support the foot of the user;

a tray extending from the footrest; and a camera mount device comprising:

a rail mount assembly comprising:

an elongated rail mount bracket having a fastening portion supported by the tray and a rail attachment portion extending from the fastening portion;

an elongated, curved or arcuate camera positioning rail having a concave rail side and a convex rail side, the camera positioning rail comprising:

a center rail portion supported by the rail attachment portion of the rail mount bracket of the rail mount assembly;

a pair of side rail portions extending from the center rail portion; and a pair of rail ends terminating the pair of side rail portions, respectively; and a camera carriage comprising:

a carriage support bracket supported by and configured to traverse the camera positioning rail; and a camera mount bracket supported by the carriage support bracket, the camera mount bracket configured to hold an electronic device having a camera with the camera facing the footrest, the footrest, the tray and the camera mount device disposed within an imaging plane; and wherein the support stand is adjustable such that the imaging plane coincides with a horizontal plane or slopes with respect to the horizontal plane upwardly from the footrest to the camera mount device.

9. The foot care apparatus of claim 8 wherein the camera mount bracket is tiltable relative to the carriage support bracket.

10. The foot care apparatus of claim 8 further comprising a device mount bracket fastener configured to attach the fastening portion of the rail mount bracket to the tray.

11. The foot care apparatus of claim 8 further comprising at least one rail groove in the camera positioning rail and at least one carriage wheel on the camera carriage, the at least one carriage wheel engaging the at least one rail groove.

12. The foot care apparatus of claim 11 wherein the at least one rail groove comprises a first rail groove and a second rail groove in opposite surfaces of the camera positioning rail, and the at least one carriage wheel comprises a first carriage wheel and a second carriage wheel engaging the first rail groove and the second rail groove, respectively.

13. The foot care apparatus of claim 8 wherein the concave rail side of the camera positioning rail faces the tray.

14. The foot care apparatus of claim 8 wherein the camera mount bracket of the camera carriage comprises a base bracket portion supported by the carriage support bracket, a base bracket portion flange extending from the base bracket portion, an adjustable bracket portion extendable and retractable with respect to the base bracket portion and an adjustable bracket portion flange extending from the adjustable bracket portion.

15. The foot care apparatus of claim 8 wherein the camera mount bracket is rotatably mounted with respect to the carriage support bracket.

* * * * *